United States Patent
Hedberg

(10) Patent No.: US 7,909,993 B2
(45) Date of Patent: Mar. 22, 2011

(54) CENTRIFUGAL FRACTION COLLECTION SYSTEM AND METHOD

(75) Inventor: Herbert J. Hedberg, North Attleboro, MA (US)

(73) Assignee: Modular SFC, LLC, North Attleboro, MA (US)

( * ) Notice: Subject to any disclaimer, the term of this patent is extended or adjusted under 35 U.S.C. 154(b) by 825 days.

(21) Appl. No.: 11/901,817

(22) Filed: Sep. 19, 2007

(65) Prior Publication Data

US 2008/0164194 A1 Jul. 10, 2008

Related U.S. Application Data

(60) Provisional application No. 60/879,385, filed on Jan. 9, 2007.

(51) Int. Cl.
*B01D 15/08* (2006.01)
(52) U.S. Cl. .............. 210/198.2; 210/512.1; 96/216; 422/553
(58) Field of Classification Search .......... 210/635, 210/656, 659, 198.2, 512.1; 95/261; 96/216; 422/101
See application file for complete search history.

(56) References Cited

U.S. PATENT DOCUMENTS

| | | | | |
|---|---|---|---|---|
| 2,986,280 A * | 5/1961 | Magnuson et al. | ........ | 210/198.3 |
| 3,395,093 A * | 7/1968 | Liberti Paula | ................ | 204/606 |
| 3,732,982 A * | 5/1973 | Dunnill et al. | ............. | 210/198.3 |
| 3,775,309 A * | 11/1973 | Ito et al. | .......................... | 210/635 |
| 3,856,669 A * | 12/1974 | Ito et al. | .......................... | 210/635 |
| 3,994,805 A * | 11/1976 | Ito | .................................. | 210/635 |
| 4,139,458 A * | 2/1979 | Harrison | ........................ | 210/657 |
| 4,341,342 A * | 7/1982 | Hara | ................................ | 494/16 |
| 4,422,941 A * | 12/1983 | Vaughan et al. | ............... | 210/657 |
| 4,900,446 A * | 2/1990 | Anderson | ....................... | 210/657 |
| 5,084,133 A * | 1/1992 | Guy et al. | ..................... | 159/47.1 |
| 5,124,023 A * | 6/1992 | Bosserman et al. | ............. | 208/99 |
| 5,601,707 A | 2/1997 | Clay et al. | | |
| 5,614,089 A | 3/1997 | Allington et al. | | |
| 5,723,050 A * | 3/1998 | Unger et al. | .................... | 210/772 |
| 6,086,767 A | 7/2000 | Walters et al. | | |
| 6,309,541 B1 | 10/2001 | Maiefski et al. | | |
| 6,413,428 B1 | 7/2002 | Berger et al. | | |
| 6,576,137 B1 * | 6/2003 | Ma | ................................... | 210/657 |
| 6,979,402 B1 * | 12/2005 | Sprague et al. | ............. | 210/198.2 |
| 7,351,333 B2 * | 4/2008 | Hawes et al. | ............... | 210/198.2 |
| 2002/0132354 A1 * | 9/2002 | Downs et al. | .................... | 436/45 |
| 2006/0101664 A1 * | 5/2006 | Lee-Smith | ........................ | 34/403 |

* cited by examiner

*Primary Examiner* — Ernest G Therkorn
(74) *Attorney, Agent, or Firm* — Cesari and McKenna, LLP

(57) ABSTRACT

A centrifugal fraction collection system including a rotating carrier for holding at least one sample collection container and inducing a centrifugal force, a guide disposed on the rotating carrier, and a flexible eluant tube disposed over the rotating carrier and through the guide for receiving a flow of eluant having volatile and non-volatile components and directing the flow of eluant into at least one sample collection container wherein the centrifugal force separates the non-volatile and volatile components based on their respective densities and collects the non-volatile components in at least one sample collection container.

23 Claims, 18 Drawing Sheets

FRACTION COLLECTOR INTERFACE TO TYPICAL
SUPERCRITICAL FLUID CHROMATOGRAPHY SYSTEM

CENTRIFUGAL FRACTION COLLECTION SYSTEM AND METHOD

RELATED APPLICATIONS

This application claims benefit of and priority of U.S. Provisional Patent Application Ser. No. 60/879,385, filed Jan. 9, 2007, incorporated by reference herein.

FIELD OF THE INVENTION

This invention relates to a centrifugal fraction collection system and method.

BACKGROUND OF THE INVENTION

The use of supercritical fluids in industrial processes has been growing at an ever-quickening pace. Replacing traditional, often hazardous and flammable, organic solvents with supercritical fluids has been a prime area of research. Carbon dioxide is a popular choice due to the fact that it is nontoxic, nonflammable, and inexpensive. An attractive feature of a supercritical fluid is that its density can be varied simply by changing the pressure or temperature. Therefore, all density-dependent properties, such as dielectric constant and solubility parameter, can be manipulated in this manner. These key features of supercritical fluids make them ideal candidates for use in extraction and chromatography applications.

In the chemical and pharmaceutical industries, the demand for purified compounds is increasing steadily. It has become highly desirable to obtain components of the highest available purity in the largest quantities. In many instances, high performance liquid chromatography (HPLC) has been the analytical method of choice for these types of separations. HPLC can be analytical or preparative in nature with the component levels varying depending on the application. In the case of preparative HPLC, a collection means is also employed for the sample fractions. However, a drawback to the use of HPLC is the fact that in many instances long elution times, as well as large of amounts of solvents are required for the process.

Supercritical fluid chromatography (SFC) was introduced in the 1980's as an alternative to HPLC. The technique employs a supercritical fluid, typically carbon dioxide, as the mobile phase. In many instances, an organic solvent is also present as a modifier in order to adjust the polarity of the mobile phase. Because supercritical fluids are known for their high diffusivities, this results in enhanced speeds and resolving power when compared to HPLC. The difference can be as much as an order of magnitude in some applications. Additionally, SFC systems can re-equilibrate faster than HPLC systems and therefore can be ready to process other samples in a shorter time frame. Many of the advantages of SFC over HPLC are applicable to both analytical and preparative methods. However, much like HPLC, SFC also needs a means to collect the sample fractions, preferably multiple fractions, in an efficient, cost-effective manner.

Conventional collection systems and methods for SFC have been explored in detail. For example, U.S. Pat. No. 6,413,428 to Berger et al. and European Patent Application No. 117057 to Berger et al., each incorporated by reference herein, disclose a sample collection process for preparative SFC using a collection chamber comprising test tubes. Sample collection methods and systems for SFC are also disclosed in U.S. Pat. No. 5,601,707 to Clay et al., U.S. Pat. No. 6,086,767 to Walters et al., U.S. Pat. No. 6,309,541 to Maiefski et al., and U.S. Pat. No. 5,614,089 to Allington et al., each incorporated by reference herein. While there are several mechanisms for analyte collection in SFC disclosed in the aforementioned patents, the collection systems and methods disclosed therein inefficiently collect fractions, are typically large, complex, difficult to operate, expensive, do not operate at room temperature and standard pressure, typically have a small number of collection tubes, and often require a chemical fume hood.

BRIEF SUMMARY OF THE INVENTION

It is therefore an object of this invention to provide a centrifugal fraction collection system and method.

It is a further object of this invention to provide such a system and method which can be integrated with conventional SFC systems.

It is a further object of this invention to provide such a system and method which is less complex.

It is a further objection of this invention to provide such a system and method which is less expensive.

It is a further object of this invention to provide such a system and method which recovers more of the sample in a supercritical eluant.

It is a further object of this invention to provide such a system and method which has higher fraction resolution.

It is a further object of this invention to provide such a system and method which operates at room temperature and atmospheric pressure.

It is a further object of this invention to provide such a system and method which is more robust.

It is a further object of this invention to provide such a system and method which is user friendly.

It is a further object of this invention to provide such a system and method which eliminates the need to enclose the system in a chemical fume hood.

It is a further object of this invention to provide such a system and method which has a smaller footprint.

It is a further object of this invention to provide such a system and method which is small relative to the number of fraction tubes.

It is a further object of this invention to provide such a system and method which provides convenient fraction recovery.

It is a further object of this invention to provide such a system and method which utilizes conventional test tubes.

It is a further object of this invention to provide such a system and method which eliminates the need for pressurized steel collection containers or steel cassettes having glass collection containers in a pressurized environment.

The invention results from the realization that an easy to use, inexpensive, compact centrifugal fraction collection system and method that operates at room temperature and atmospheric pressure, and provides a relatively high numbers of fraction collection containers, e.g., 12 or more, is effected, in one embodiment, with a rotating carrier in an enclosure for holding a plurality of sample collection containers and inducing a centrifugal force. A flexible eluant tube disposed through a guide mounted to the rotating carrier receives and dispenses a flow of eluant having volatile and non-volatile compounds. The eluant, preferably flowing under pressure from a connection to a separation system, such as an SFC system, is sprayed from the end of the eluant tube into a desired collection container wherein the centrifugal force, separates the non-volatile compounds from the volatile compounds based on their respective densities. The higher density non-volatile compounds are collected in the desired collection container while the lower density volatile compounds escape into the enclosure.

The subject invention, however, in other embodiments, need not achieve all these objectives and the claims hereof should not be limited to structures or methods capable of achieving these objectives.

This invention features a centrifugal fraction collection system including a rotating carrier for holding at least one sample collection container and inducing a centrifugal force, a guide disposed on the rotating carrier, and a flexible eluant tube disposed over the rotating carrier and through the guide for receiving a flow of eluant having volatile and non-volatile components and directing the flow of eluant into at least one sample collection container. The centrifugal force separates the non-volatile and volatile components based on their respective densities and collects the non-volatile components in at least one sample collection container.

In one embodiment, one end of the flexible eluant tube may be configured to receive the flow of eluant from a supercritical fluid chromatography system. One end of the flexible eluant tube may be maintained in a fixed position above the rotating carrier and the other end of the flexible eluant tube axially rotates in the guide. The system may include a plurality of sample collection containers disposed in the rotating carrier. The system may include a distributor subsystem coupled to and synchronized with the rotating carrier for locating, aligning, and locking the flexible eluant tube to a predetermined one of the plurality of sample collection containers and for distributing fractions of the eluant to a predetermined number of the plurality of sample collection containers. The next predetermined sample collection container in the collection sequence may be located approximately opposite a sample collection container receiving a flow of eluant and for maintaining a symmetrical distribution of weight of collected eluant among the plurality of sample collection containers. The distributor subsystem may advance the guide and flexible eluant tube to each of the plurality of sample collection containers in a predetermined pattern for maintaining a symmetrical distribution of weight of the fractionated eluant in the plurality of sample collection containers. The distributor subsystem may include a distributor cover having one or more detent recesses, an actuator, one or more rotating pawls, and a clutch mechanism. The actuator may be coupled to the rotating carrier and the one or more rotating pawls may engage the one or more detent recesses in the distributor cover to lock the distributor cover at a desired location. The distributor subsystem may include a distributor cover having a plurality of locking teeth and one or more locking pins or levers which engage one or more of the plurality of locking teeth to halt the distributor cover at a desired location and counteract accumulated angular momentum generated by rotating the distributor cover. A profile of the one or more detent recesses in the distributor cover may align the distributor cover, the guide, and the flexible eluant tube proximate a predetermined one of the plurality of sample collection containers. The distributor subsystem may be advanced to the next predetermined sample collection container mechanically and/or electrically by applying pneumatic pressure pulses and/or by applying mechanical forces and/or by applying electrical signals and/or by applying optical signals and/or by applying wireless signals and/or by applying electromagnetic signals. The flexible eluant tube may extend a predetermined length into a sample collection for increasing the yield of the non-volatile components. The system may include a retraction device for retracting the flexible eluant tube from one of the plurality of collection containers while the distributor subsystem advances to the next predetermined one of the plurality of sample collection containers. The retraction device may be controlled mechanically and/or electrically by applying pneumatic pressure pulses and/or by applying mechanical forces and/or by applying electrical signals and/or by applying wireless signals and/or by applying optical signals and/or by applying electromagnetic signals. The system may include a collection container identification subsystem for determining the location of one of the plurality of sample collection containers receiving the flow of eluant. The system may include a diverter valve coupled between a source of the flow of eluant and the flexible eluant tube configured to temporarily stop the flow of eluant while the retraction device retracts the flexible eluant tube and the distributor subsystem advances the flexible eluant tube to the next predetermined sample collection container and extends the flexible eluant tube into a next predetermined sample collection container and thereafter allowing the flow of eluant to be dispensed in the next predetermined sample collection container. The volatile components may include carbon dioxide and the non-volatile compounds include a component chosen from the group consisting of: molecules, compounds, chiral molecules, enantiomers, drugs, sample precipitates, reactants, reaction products, natural product extracts, and modifier solvents. The flexible eluant tube may be made of a durable material capable of withstanding continuous flexing caused by high speed rotation of the rotating carrier, and which is un-reactive with the volatile and non-volatile components. The system may include an embedded controller for controlling the distributor subsystem, the retraction device, the collection container identification subsystem, the diverter valve, and the rotation speed of the rotating carrier by predetermined commands entered into the controller or by commands received from an external system control subsystem. The controller may include a control panel having a display for displaying the sample collection container receiving the eluant and a plurality of switches for controlling operation of the rotating carrier, the distributor subsystem, the diverter valve, and for programming collection of pure compounds from the non-volatile components into one or more of the plurality of collection containers based on a commands entered into the controller and/or signals from a chemical processing system detector and/or from the control computer of a chemical processing system.

This invention also features a centrifugal fraction collection system including a rotating carrier for holding at least one sample collection container and inducing a centrifugal force, and an eluant tube disposed over the rotating carrier and coupled to the rotating carrier for receiving a flow of eluant having volatile and non-volatile components and directing the flow of eluant into at least one sample collection container. The centrifugal force separates the non-volatile and volatile components based on their respective densities and collects the non-volatile components in at least one sample collection container.

In one embodiment, the system may include a housing, a cover, and a fluidic sealing bearing disposed in the cover, the fluidic sealing bearing including a coupling attached to a rigid eluant tube receiving the flow of eluant and a rotating portion disposed in the coupling fixably attached to a rigid eluant tube which is fixably attached to the rotating carrier.

This invention further features a method for centrifugal fraction collection including providing a flow of eluant having non-volatile components and volatile components, providing a rotating carrier for holding one or more sample collection containers, providing a flexible eluant tube receiving the flow of eluant inducing a centrifugal force on a rotating carrier, and wherein the centrifugal force separates the non-volatile components from the volatile components based on their respective densities and collects the non-volatile components in the one or more sample collection containers.

This invention also features a flash supercritical chromatography system and centrifugal fraction collector subsystem, including a source of supercritical fluid solvent, and a source of organic modifier solvent, and a source of eluant having non-volatile components and volatile components therein. A selector valve coupled to the source of supercritical solvent and the source of organic modifier provides a pressurized flow of the eluant. A mixer coupled to the selector valve receives the pressurized flow of eluant and for mixing periodic boluses of alternating supercritical solvent and organic modifier. An injector subsystem injects a sample into the pressurized flow of eluant. A chromatography column coupled to the injector receives the pressurized flow of eluant. A phase transition tube reduces the pressure of the flow of eluant. A fraction collection subsystem includes a rotating carrier for holding at least one sample collection container and inducing a centrifugal force, a flexible eluant tube disposed above the rotating carrier and coupled to the rotating carrier and/or through a guide on the rotating carrier for receiving the flow of eluant at the reduced pressure, and wherein the centrifugal force separates the volatile and non-volatile components of the eluant based on their respective densities and collects the non-volatile components in the at least one sample collection container.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
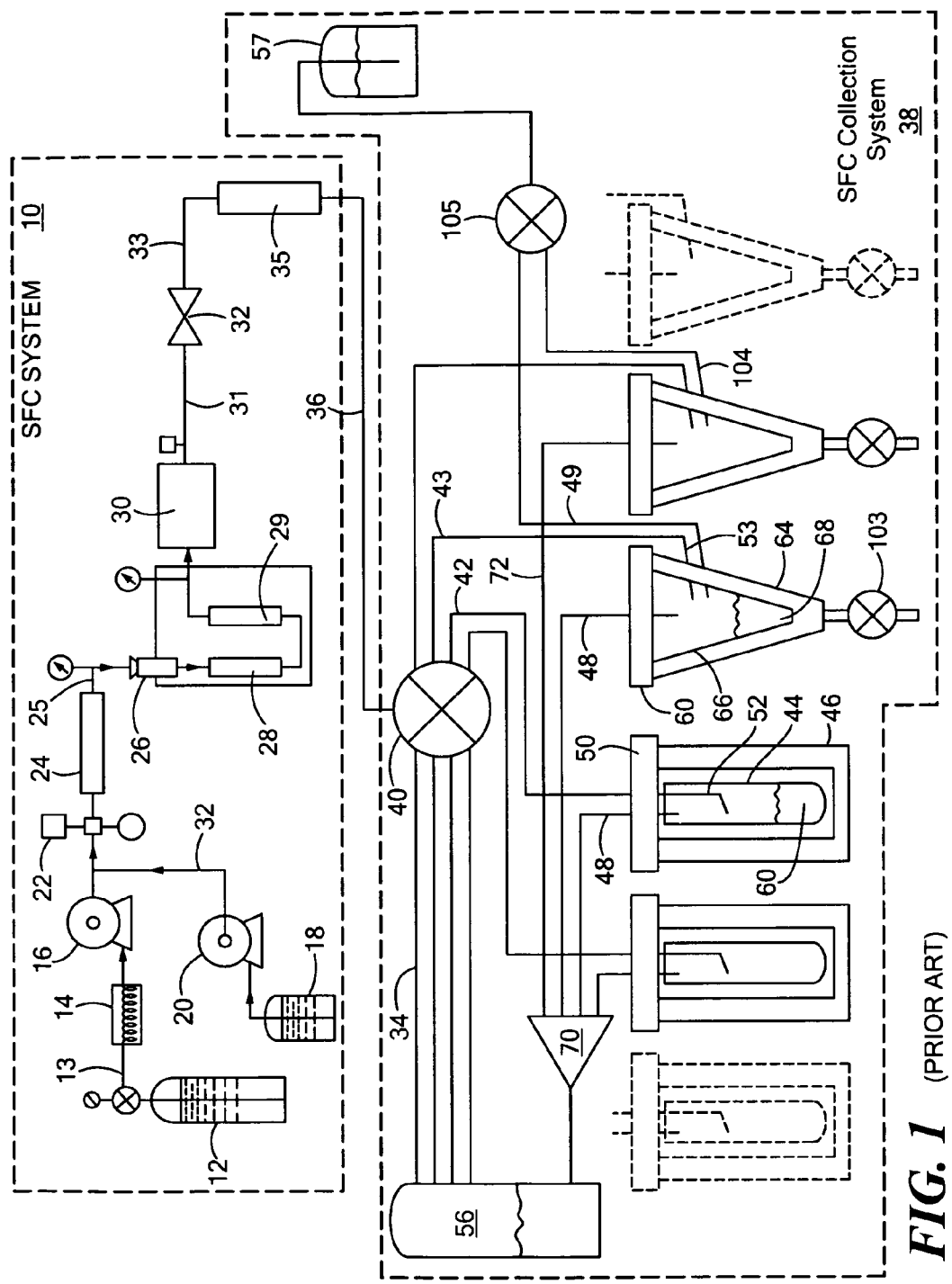
FIG. 1 is a schematic block diagram of a typical conventional SFC system.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

Typical conventional SFC system 10, FIG. 1, is a packed-column SFC system. System 10 typically includes a carbon dioxide supply tank 12, line chiller 14, pump 16, organic solvent modifier tank 18, pump 20, and dampener and pressure transducer 22 coupled to a mixing column 24 connected to injection valve 26. Injection valve 26 is connected to at least one packed chromatography column 28, 29, which is connected to detector 30.

In a typical SFC system, such as SFC system 10, liquefied compressed carbon dioxide gas is supplied from $CO_2$ supply tank 12. High pressure tubing 13 connects $CO_2$ supply tank 12 to pump 16. The tubing may be cooled by line chiller 14 prior to connecting to pump 16. In this example, system 10 uses two HPLC-type reciprocating pumps 16 and 20. Pump 16 delivers $CO_2$ to transducer 22 coupled to mixing column 24 and pump 20 delivers modifier solvent 18, e.g., methanol, to transducer 22 coupled to mixing column 24. The $CO_2$ and modifier are combined in mixing column 24 to create a mixture of modifier dissolved into the supercritical fluid in transfer tubing 25.

The combined supercritical fluid is pumped at a controlled mass-flow rate from the mixing column 24 through transfer tubing 25 to fixed-loop injector 26 where the sample of interest is injected into the solvent flow path. The sample combines with the pressurized supercritical and modifier fluids inside the injection valve 26 and is carried into at least one packed chromatography column 28 and 29. After separation of the sample occurs into distinct pure compound regions in the columns 28 and/or 29, the elution flow passes from the column outlet into detector 30. Back pressure regulator 32 is used to regulate the system pressure and the flow rate of the eluant in line 31.

A plurality of heaters (not shown) may be mounted in series on line 33 to heat the elution fluid after the backpressure regulator 32. The elution fluid is heated to within the control temperature of evaporator 35, which is typically between 5° to 50° C., to protect heat sensitive compounds in the elution flow from being damaged. The objective of evaporator 35 is to boil $CO_2$ out of the elution components as the mixture passes through the evaporator 35 and to suppress aerosol formation within transfer tube 36. Transfer tube 36 also insures a high enough backpressure to prevent the liquid carbon dioxide from forming solid carbon dioxide, also known as dry ice. The restriction increases the backpressure in the heated zone in line 33 and reduces the amount of the gas expansion.

Conventional SFC collection system 38 includes a fraction selection valve 40, which is coupled between transfer tube 36 and inlet transfer tubes 42, 43. Inlet transfer tubes 42, 43 carry the elution flow in liquid and gaseous phases into disposable collection vials 44 housed in collection cassette chamber 46 and reusable chamber 66 which is an integral part of cyclone separator 64, respectively. Inlet tube 42 fits through a hole in lid 50 and inlet tube 43 fits through a hole in side of chamber 64 and insert into disposable collection vial 44 and reusable collection chamber 66 respectively. Proper fittings on inlet tubes 42, 43 provide airtight connections that can withstand the high pressure forces of SFC system 10, e.g., 20 to 100 p.s.i., to limit the volume of the expanding $CO_2$ gas. Inlet tube probes 52, 53 direct elution fluid into collection vial 44 and chamber 66 and outlet tubes 48, 49 provide a vent for gas that is under pressure to exit cassette chamber 46 and cyclonic separator chamber 64 and discharge to waste collection container 56.

Fractions may be collected in disposable collection vial 44 in chamber 46 or in tapered reusable collection reservoir 66 interior to chamber 64. During the fractionation process, both the liquid phase and the gas phase of the elution flow discharge into the collection vial 44, 66 where the liquid phase is supposed to remain in the collection reservoirs and the gas phase is supposed to vent through outlet tubing 48, 49. The pressurization of the collection chamber 46, 64 serves to minimize the volume of $CO_2$ which decreases the velocity the $CO_2$ and the atomization of the liquid phase within the chamber 46, 64. This in turn reduces the magnitude of shear forces occurring between the $CO_2$ gas and the collected liquid at the bottom of the collection vials 44, 66, as shown at 60, 68, respectively. With lower shear forces, there is less tendency for the collected liquid to become an aerosol and be removed from the collection vials 44, 66 with the exiting gas. An additive beneficial effect is obtained by the proper angling the tube outlets 52, 53 relative to the walls of collection vial 44 and collection container 66. The closer the angle of the tube outlets 52, 53 is to horizontal, the lower the observed turbulence at the liquid surface. However, enough angle must be provided to insure the majority of effluent is directed downward rather than upward on the walls of disposable collection vial 44 and reusable collection container 66.

Outlet tube 48 from chamber 46 and outlet tube 49 from chamber 64 are connected to fixed restrictor 70 in order to keep high pressure inside the chambers 44, 64. Fixed restrictor 70 raises the upstream pressure which may be set to between approximately 20 and 100 p.s.i., depending on $CO_2$ flow rate and to minimize atomization of the liquid phase. To increase laboratory safety, collection system 38 should ideally not have any exposure of waste effluent, samples, or vented $CO_2$ to ambient laboratory air. The liquids and gasses in system 38 remain in a contained system that can be directed to a hood or safety exhaust to maximize safety for the technician. See, e.g., the patents to Berger et al. cited supra. The result is collection system 38 typically has a low fraction container count, is large, complex, expensive, difficult to operate, often occupies space in a chemical fume hood, and operates at high pressure.

Figure 2:
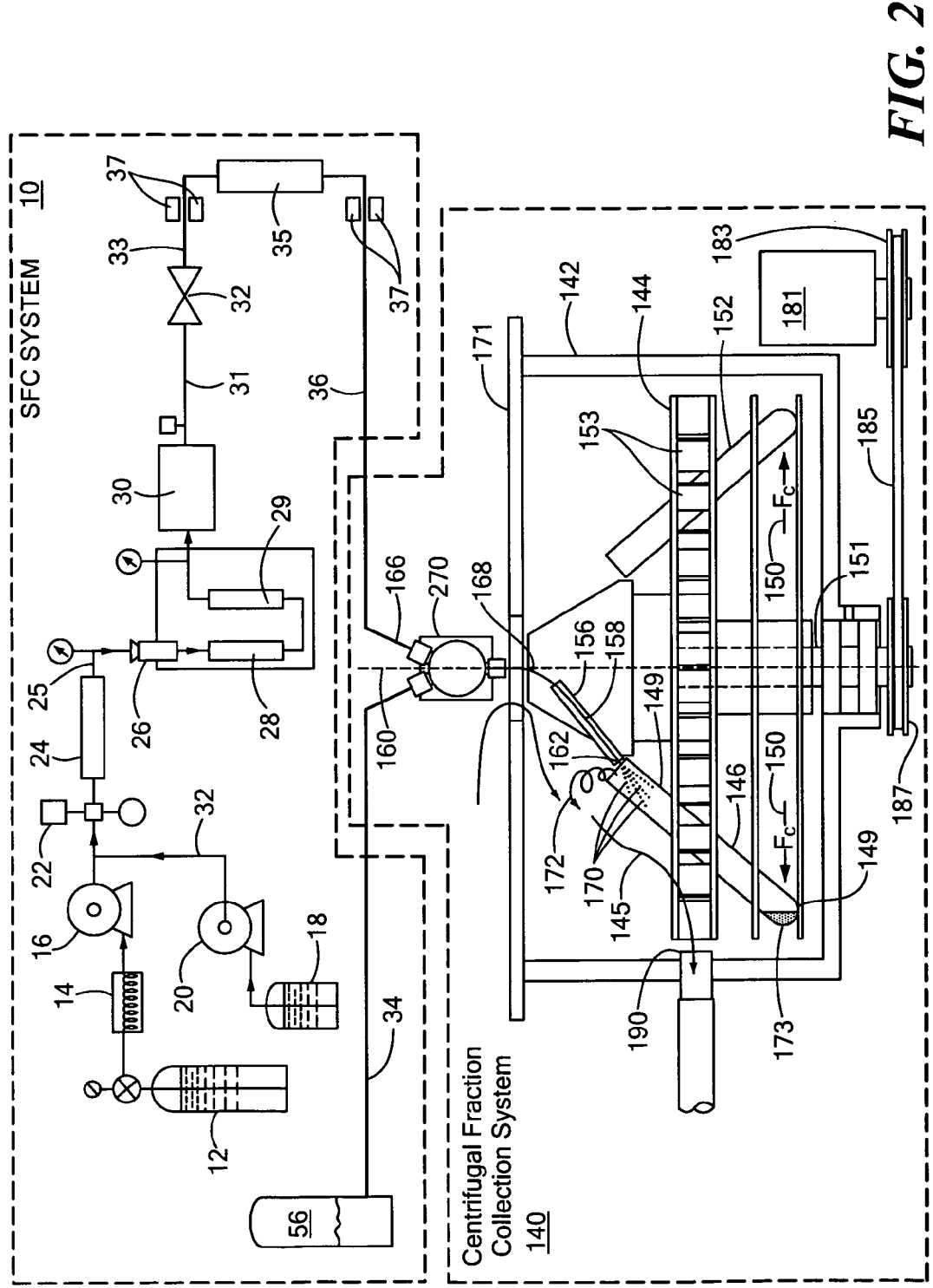
FIG. 2 is a schematic side view of one embodiment of the centrifugal fraction collection system of this invention coupled to the conventional SFC system in FIG. 1.

In contrast, centrifugal fraction collection system 140, FIG. 2, of this invention, where like parts have been given like numbers, includes rotating carrier 144, preferably disposed in housing 142, for holding at least one sample collection container 146. Rotating carrier 144 rotates and induces a centrifugal force $F_c$ 150. In one embodiment, centrifugal fraction collection system 140 may include a plurality of sample collection containers, e.g., 12, 24, or 36, or any number of containers where one half of the number of collection containers is an even number of collection containers (discussed in further detail below). One additional collection container is depicted by sample collection container 152. In one design, guide 156 is disposed on rotating carrier 144. Flexible eluant tube 158 is preferably disposed over center axis 160 of rotating carrier 144 at end 168 and extends through guide 156 with end 162 located inside sample collection container 146.

Flexible eluant tube 158 receives a flow of eluant having volatile components and non-volatile components (e.g., a mixture of $CO_2$ and modifier solvent into which are dissolved concentrated pure regions of separated sample) from a source, e.g., connection 166 to tube 36 coupled to SFC system 10, similar as discussed with reference to FIG. 1. Diverter valve 270, FIG. 2, diverts the flow of eluant in tube 36 to end 168 of flexible eluant tube 158 or to waste collection container 56 (discussed in detail below). Back pressure regulator 32 of SFC system 10 is configured to provide the desired liquid flow rate through column 28, 29 and delivers the flow of eluant to the tubes 33, 36. Over the length of tubes 33, 36 the eluant pressure drops from a pressure of at least about 1,000 p.s.i. to about atmospheric pressure of 14.7 p.s.i. This pressure provides the flow of eluant in tubes 33, 36 and is delivered to flexible eluant tube 158 via connection 166. Heaters 37 about tubes 33, 36 prevent the formation of dry ice from expanding $CO_2$ in tubes 33, 36. Thus, collection system 140 of this invention receives the source of eluant from SFC system 10 which is at about 1 atmosphere and warmed sufficiently, e.g., room temperature, to prevent freezing of the eluant mixture in the restriction tube 36.

The centrifugal force, $F_c$ 150, generated by rotating carrier 144 causes the non-volatile and volatile components in the flow of eluant sprayed from flexible eluant tube 158 to be directed into sample collection container 146, as shown by spray pattern 170. Centrifugal force, $F_c$ 150 forces the more dense non-volatile components in the flow of eluant sprayed out of flexible eluant tube 158 to the bottom of container 146, as shown at 173, while the volatile components (e.g., carbon dioxide gas) remain in sample collection container 146 and then escape into the atmosphere, e.g., into housing 142, as shown at 172, when the internal pressure of inside container 146 increases sufficiently to displace accumulated non-volatile components. Thus, centrifugal force, $F_c$ 150 separates the more dense non-volatile components from the less dense volatile components based on their respective densities.

The result is centrifugal collection system 140 of this invention relies on centrifugal force to separate the non-volatile components from the volatile components in the eluant. Thus, system 140 is less complex, less expensive, easier to operate, and utilizes less space than conventional collection systems for SFC systems. Because system 140 is operating at room temperature and about 1 atmosphere, centrifugal force $F_c$ 150 causes virtually all of the non-volatile sample compounds in the eluant flow in flexible eluant tube 158 to be captured by sample collection container 146, while the volatile components escape into the atmosphere. Therefore, the problems associated with sample loss due to atomization by the expanding volatile components are eliminated, resulting in almost complete recovery of the sample. One preliminary trial of system 140 produced a 100% yield of the sample. Therefore, system 140 provides fractionation yields at least equal to conventional collection systems for SFC. Moreover, collection system 140 accommodates a plurality of sample collection containers, e.g., 12, 24, or 36, or any even number of collection containers where half the number is an even number. The sample collection containers can be standard, off-the-shelf test tubes. This eliminates the need to use pressurized steel collection containers or steel cassettes having glass collection containers at a pressurized environment or the washing of reusable cyclonic separator vessels between samples.

In one example, the volatile components in the eluant include carbon dioxide or similar type volatile components, e.g., the volatile components as disclosed in U.S. Pat. No. 6,908,507, incorporated by reference herein. The non-volatile components include solvent modifiers, e.g., methanol, molecules, compounds, chiral molecules, enantiomers, and drugs. Therefore, system 140 can separate enantiomers needed in the pharmaceutical industry.

In a preferred design, flexible eluant tube 158 is made of a desirable material capable of withstanding continuous flexing caused by the high speed rotation of the rotating carrier and is non-reactive with the non-volatile and volatile components in the eluant, e.g., chemicals used in processing. Exemplary materials for flexible eluant tube 158 may include polyamide-coated fused silica capillary, or other durable and flexible tubing known to those skilled in the art. In other designs, flexible eluant tube 158 may be made of fused silica capillary which may be coated with polyetheretheketone (PEEK) or of composed entirely of PEEK.

Rotating carrier 144 is preferably mounted on spindle 151. Motor 181 with pulley 183 and belt 185 attached to pulley 187 drives spindle 151 to rotate rotating carrier 144 to a desired speed, e.g., at about 1,500 revolutions per minute (r.p.m.), to provide the necessary rotation speed on rotating carrier 144 to establish centrifugal force $F_c$ 150. In one design, fan blades 153 in rotating carrier 144 assist in the removal of volatile gas, e.g., as shown at 172. In this design, fan blades 153 integrated into rotating carrier 144 eject volatile components (shown at 172) which accumulate in housing 142 out exhaust hose 190, shown by arrow 145, hose 190 is connected to a standard vapor extraction system. This eliminates the need to place collection system 140 in a chemical fume hood.

Figure 3A:
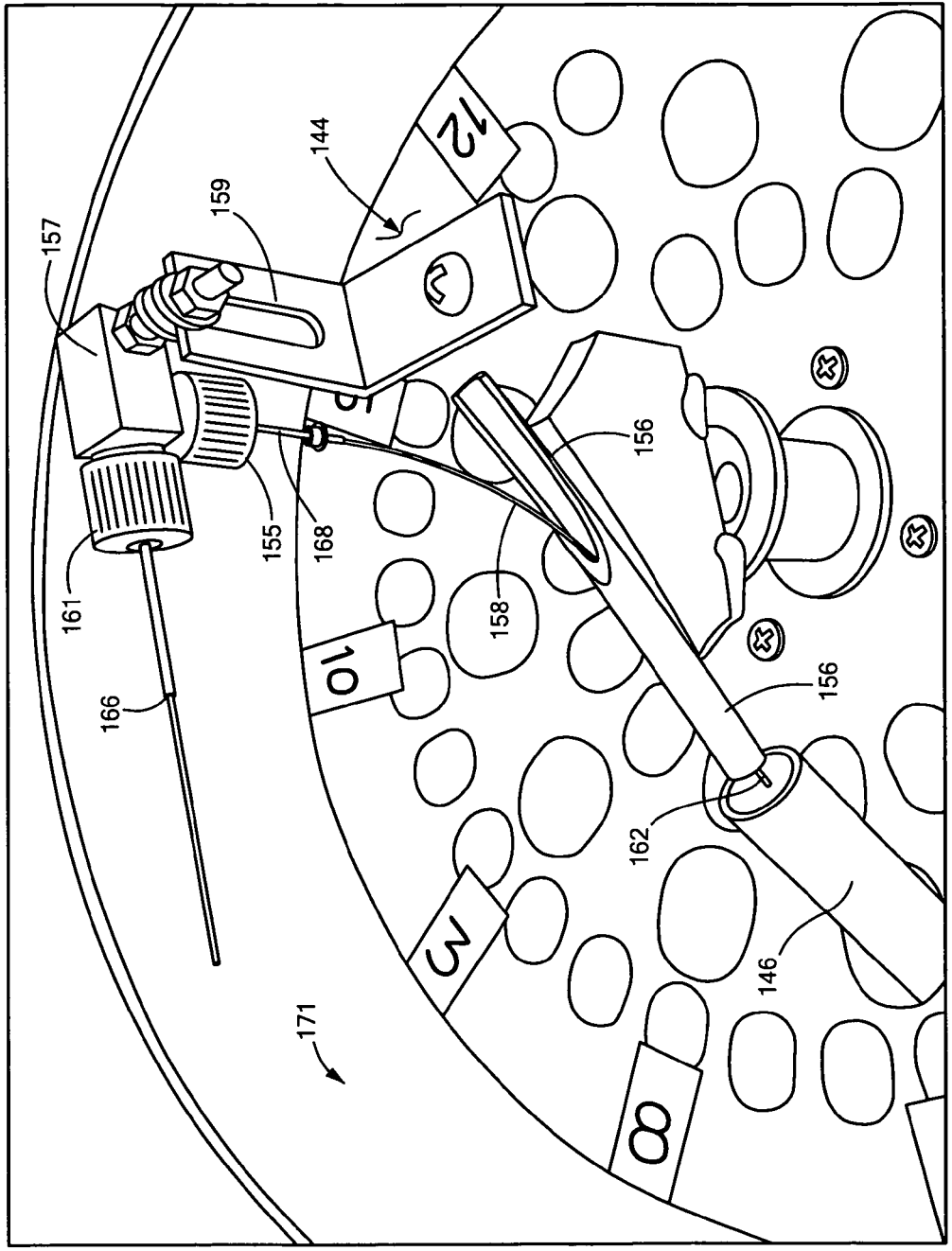
FIG. 3A is a three-dimensional side view showing in further detail of one embodiment of the flexible eluant tube disposed through the guide shown in FIG. 2.
Figure 3B:
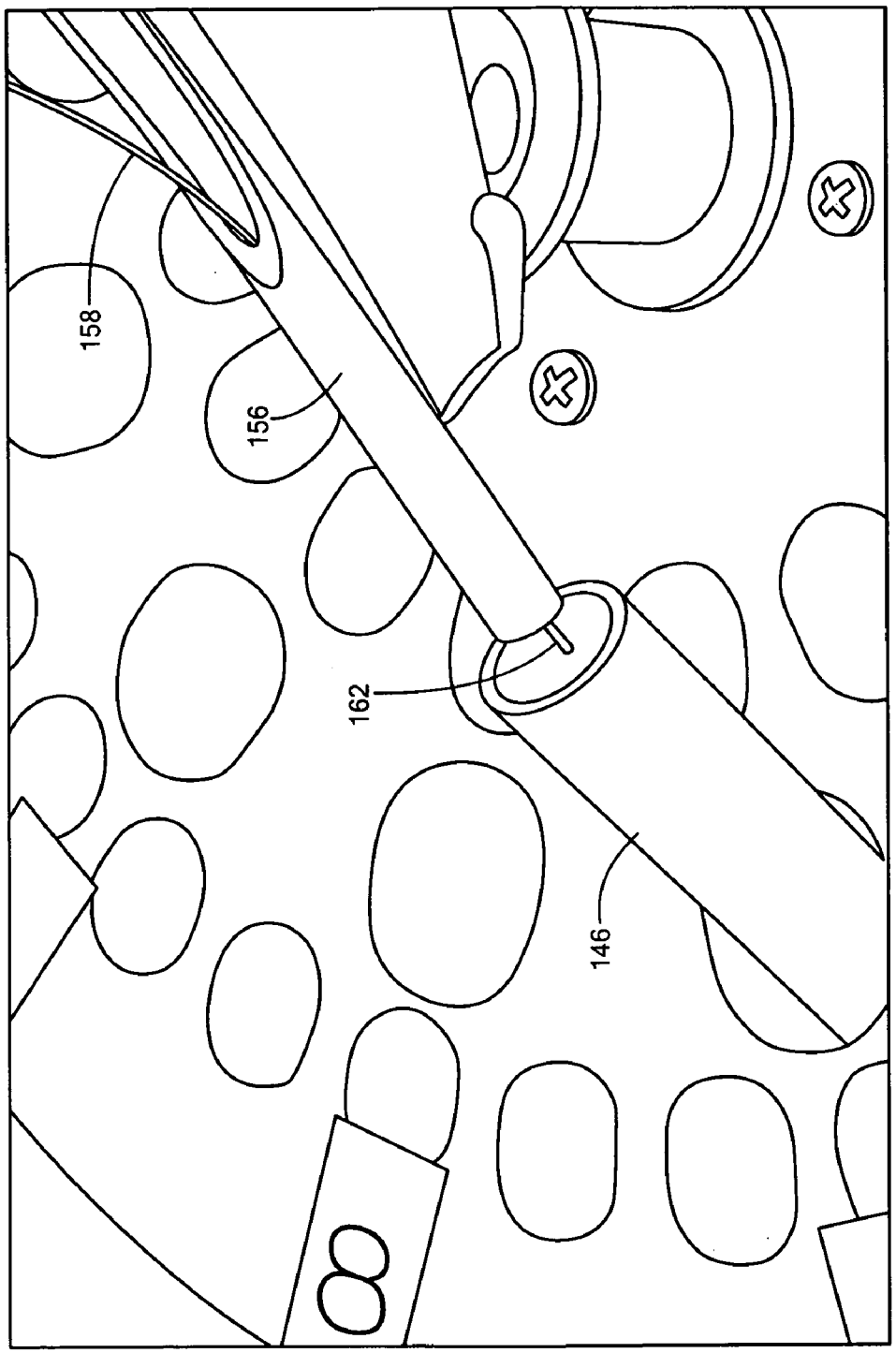
FIG. 3B is a three-dimensional side view showing in further detail one end of the flexible eluant tube extending from the guide and into the sample collection container shown in FIGS. 2 and 3A.

Ideally, end 162 of flexible eluant tubing 158, FIG. 3A, extends into sample collection container 146 to increase the yield of the non-volatile components collected in sample collection container 146. For example, end 162, FIG. 3B, may extend about 5 mm into sample collection container 146. The eluant in flexible eluant tube 158 is sprayed in a cone shaped spray pattern 170, FIG. 2, into collection container 146. The eluant will contact the wall 149 of collection container 146 as collection container 146 moves in its circular path as determined by the rotating carrier 144.

The centrifugal force, $F_c$ 150 generated by rotating carrier 144 upon the eluant spray shown at 170 causes a density separation of the non-volatile and volatile components in the eluant, as discussed above. The non-volatile sample components and modifier solvent slide down the wall 149 and are collected at the bottom of collection container 146, a shown at 173. The $CO_2$ gas pressurizes the interior of collection container 146 until it exceeds the pressure created by the centrifugal force, $F_c$ 150 on the $CO_2$ gas. When the gas pressure is exceeded, the excess $CO_2$ gas spills out of the container opening into the housing, as shown at 172 and is swept out to hose 190.

In one embodiment, end 162 of flexible eluant tube 158 is held fixed in place, e.g., by an attachment mounted on cover 171. For example, end 168, FIG. 3A of flexible eluant tube 158 may be held fixed in place by fitting 155 attached to coupler 157 on frame 159 attached to cover 171. Coupler 157 also includes fitting 161 that connects outlet tube 36 of SFC system 10, FIG. 2.

Figure 4:
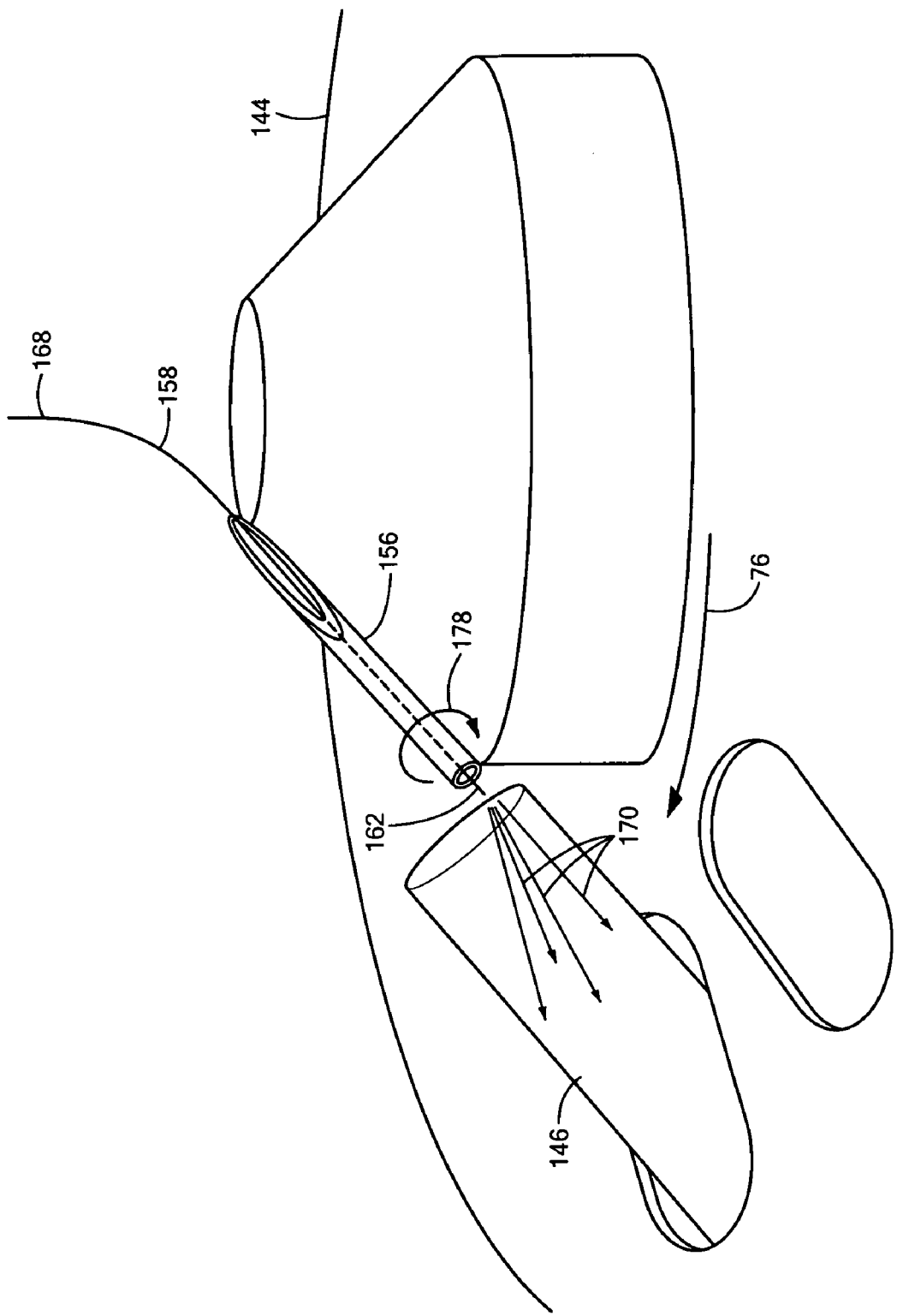
FIG. 4 is a three-dimensional view showing in further detail one example of the axial rotation of the flexible eluant tube within the guide tube shown in FIGS. 2, 3A, and 3B.

When end 168, FIGS. 2 and 3A is held in a fixed position, the rest of flexible eluant tube 158 axially rotates in the same direction as rotating carrier 144, as shown by arrow 178, FIG. 4. The high flexibility and strength of flexible eluant tube 158 allows end 168 to be held fixed in place while the rest of flexible eluant tube 158 axially rotates at speeds of up to about 1,500 r.p.m., equal to that of rotating carrier 144.

Figure 5:
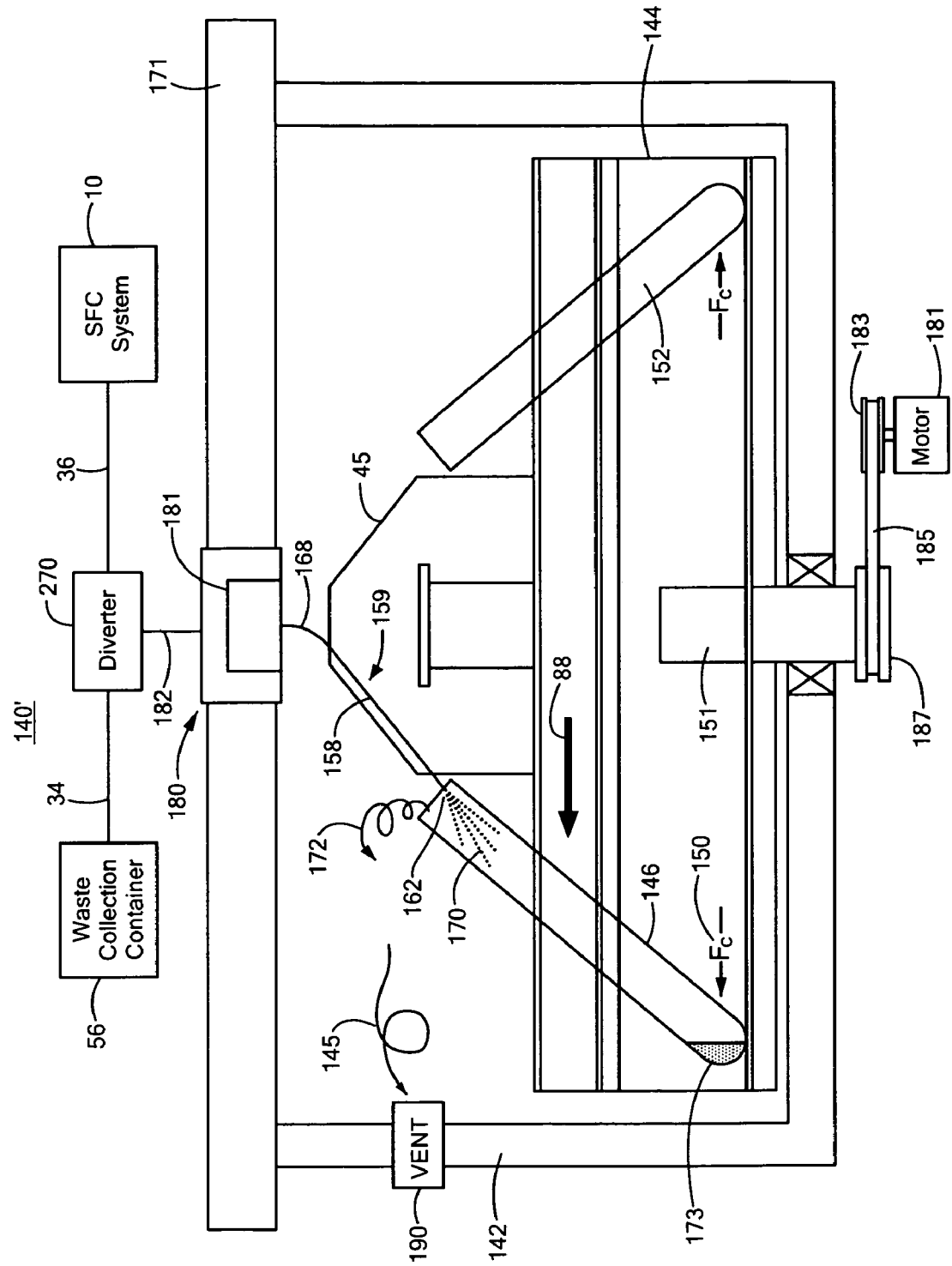
FIG. 5 is a schematic side view of another embodiment of the centrifugal fraction collection system of this invention showing one design of a fluidic bearing coupled to the eluant tube.

In another embodiment, SFC system 140', FIG. 5 of this invention, where like parts have been given like numbers, includes fluidic bearing 180. Fluidic bearing 180 receives a flow of eluant by tube 182 coupled to diverter valve 270 coupled to transfer tube 36 connected to SFC system 10, similarly discussed above with reference to FIG. 2. In this design, flexible eluant tube 158 is attached to rotating carrier 144 at section 159 and end 168 is fixed to rotating member 181 of fluidic bearing 180. When rotating carrier 144 rotates, end 168 rotates with rotating member 181 and eluant tube 158, which in this example, need not be flexible, remains stationary on rotating carrier 144. Similarly, as discussed above with reference to FIG. 2, the rotation of rotating carrier 144 establishes centrifugal force $F_c$ 150 for separating the volatile and non-volatile components in the eluant in flexible eluant tube 158 based on their respective densities and traps the non-volatile components in sample collection container 146.

Figure 6:
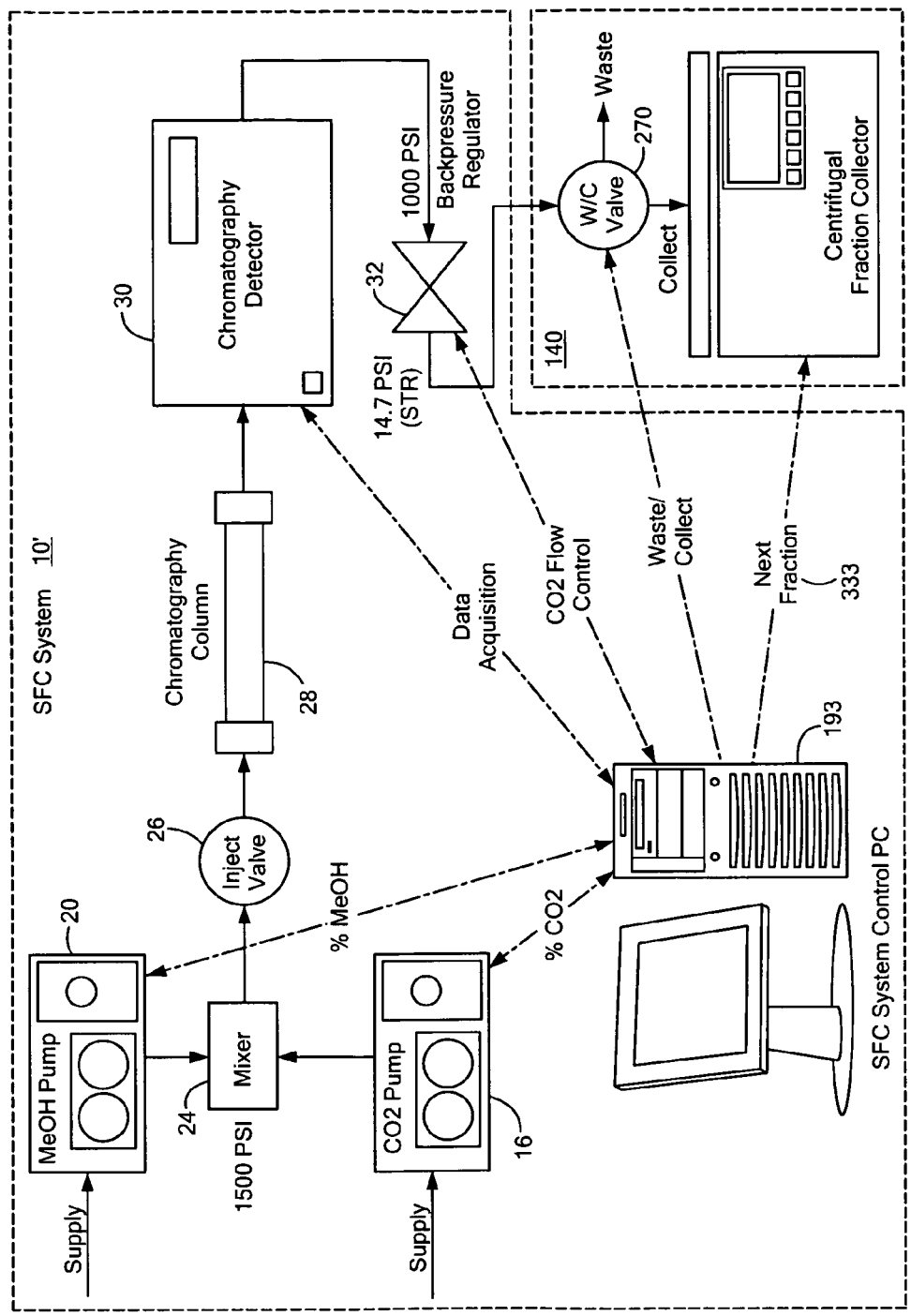
FIG. 6 is a schematic block diagram showing the primary components of an SFC system incorporating the centrifugal fraction collection system of this invention.

FIG. 6, where like parts have been given like numbers, shows one embodiment of centrifugal fraction collection system 140 of this invention coupled to SFC system 10' of similar design as SFC system 10, FIG. 1. SFC system 10', FIG. 6, includes computer subsystem 193, e.g., a personal computer, which controls the amount of carbon dioxide delivered by pump 16 and the amount of methanol delivered by pump 20 to mixer 24. Computer subsystem 193 also controls chromatography detector 30, back pressure regulator 32, and diverter valve 270 (discussed below). Computer subsystem 193 can also be used to control the fractionation of the eluant flow by centrifugal fraction collection system 140, discussed in more detail below.

Figure 7A:
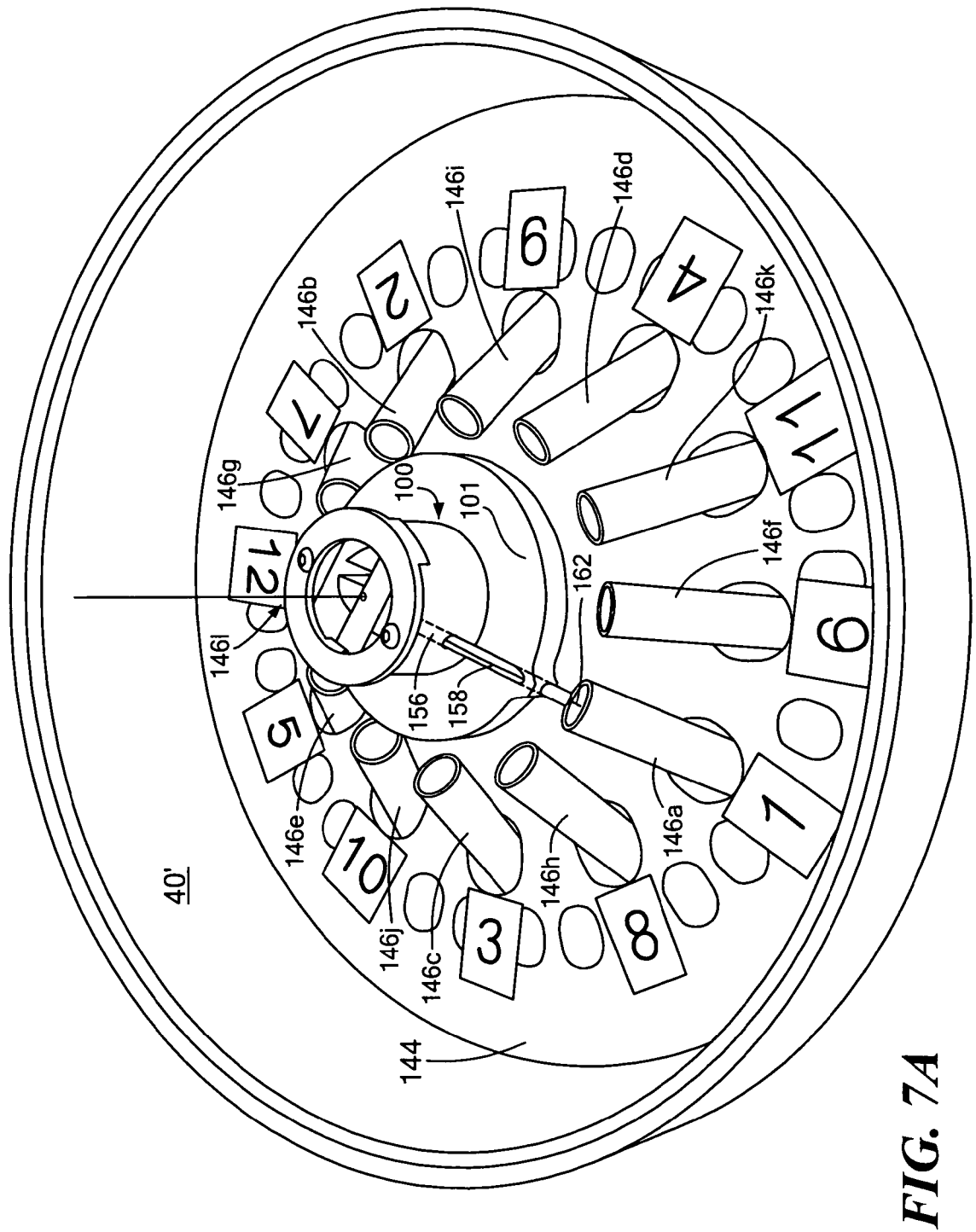
FIG. 7A is a three-dimensional top view of one embodiment of the distributor subsystem and a rotating carrier configured to hold a plurality of sample collection containers in accordance with this invention.

In one design, rotating carrier 144, FIG. 7A of centrifugal fraction collection system 140, FIGS. 2-6, holds twelve sample collection containers, e.g., 12 standard, off-the-shelf test tubes, such as sample collection containers 146a, 146b, 146c, 146d, 146e, 146f, 146g, 146h, 146i, 146j, 146k, and 146l, located in positions 1, 2, 3, 4, 5, 6, 7, 8, 9, 10, 11, and 12, respectively. In other designs, rotating carrier 144 may hold any number of containers where one half of the number of collection containers is an even number. For example, in one design, rotating carrier 144, FIG. 7B, where like parts have been like numbers, is configured to hold 24 sample containers at positions 1-24.

Figure 7B:
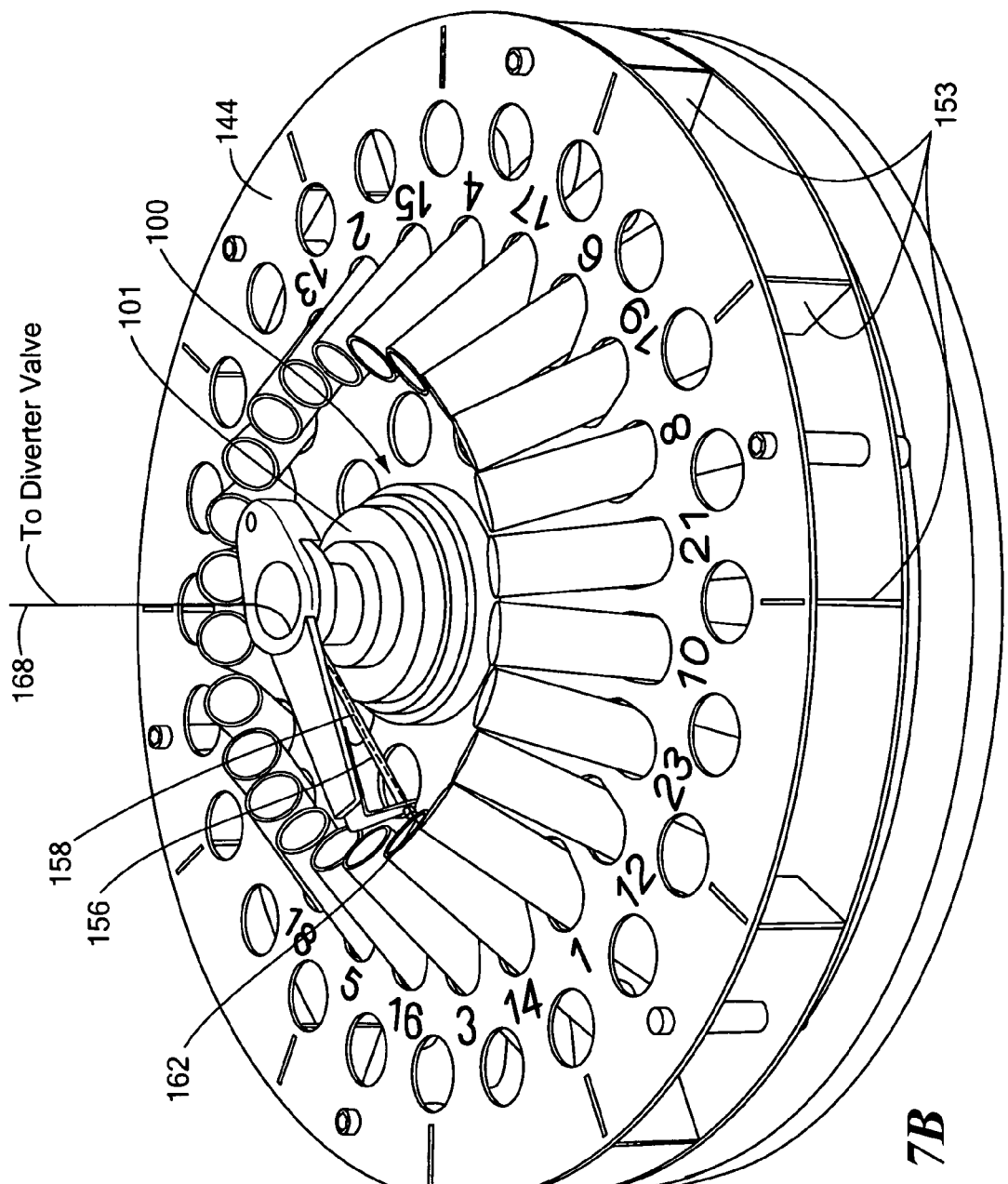
FIG. 7B is a three-dimensional top view of another embodiment of the distributor subsystem and a rotating carrier configured to hold a plurality of sample collection containers of this invention.

Because rotating carrier 144 must be spinning at high r.p.m. during operation to generate the required centrifugal force to capture the non-volatile components from the eluant, consecutive fractions cannot be collected in adjacent sample collection containers, e.g., sample collection containers 146*a* and 146*f*, FIG. 7A, because centrifugal imbalance will be result which may produce destructive vibrations. To prevent such a centrifugal imbalance, centrifugal fraction collection system 140", FIG. 8, where like parts have been given like numbers, includes distributor subsystem 100 coupled to rotating carrier 144. In this design, guide 156 is preferably attached to distributor cover 101 and flexible eluant tube 158 is disposed therethrough. FIGS. 7A and 7B show exemplary embodiments of distributor subsystem 100 with distributor cover 101 and guide 156 thereon and flexible eluant tube 158 therein disposed on rotating carrier 144. Distributor subsystem 100, FIG. 8, preferably includes actuator 102, with rotating plate 114 attached to rotor hub 104. Rotor hub 104 is coupled to spindle 151. Similar as described above, motor 181 with pulley 183 and belt 185 attached to pulley 187 drives spindle 151 so that rotating carrier 144 rotates at the desired rate, e.g., about 1,500 r.p.m., to establish the necessary centrifugal force $F_c$ 150 to separate the volatile and non volatile components in the flow of eluant, as discussed above. Distributor subsystem 100 also includes clutch mechanism 112, e.g., a Sprag-type clutch, is rotorably coupled to rotating plate 114.

Figure 8:
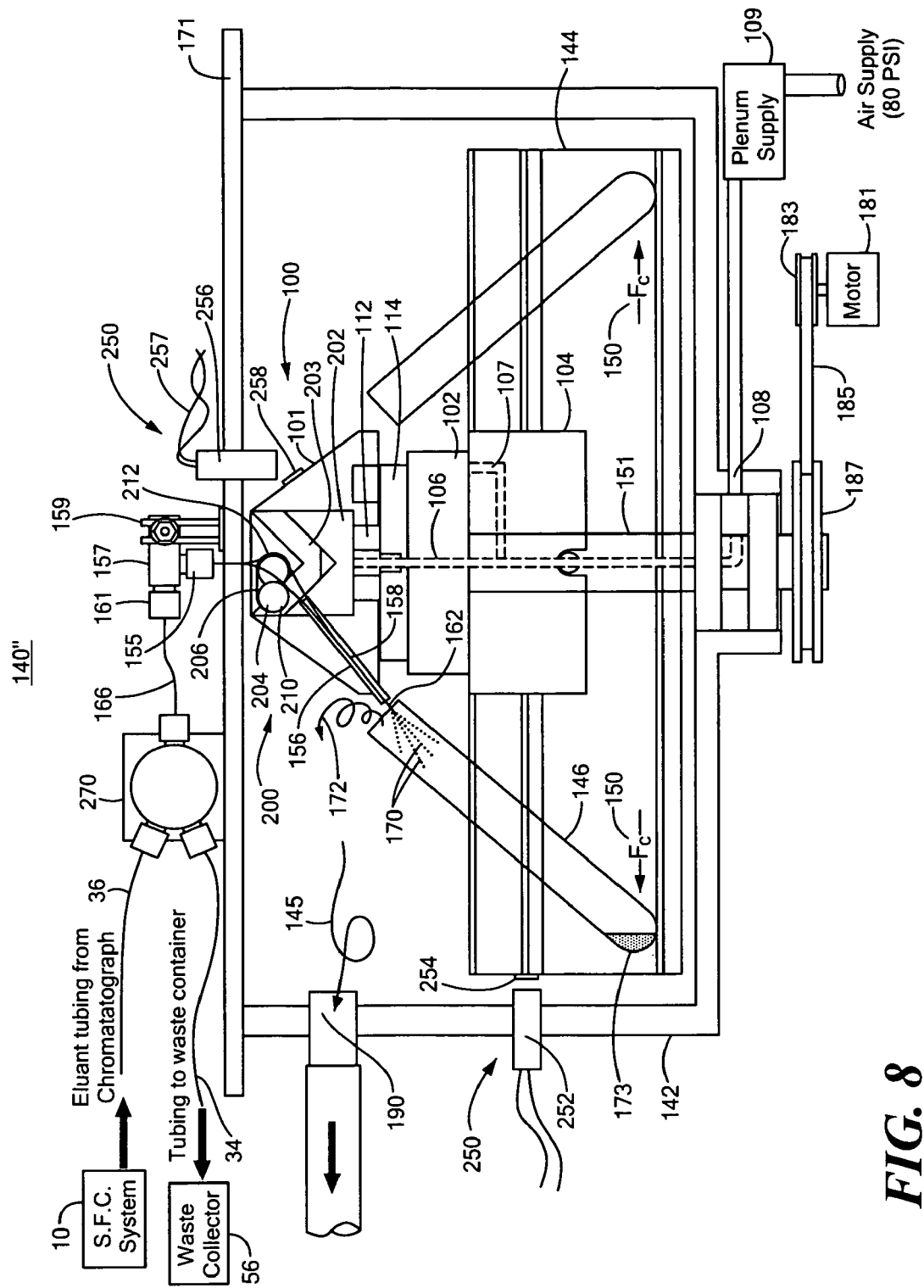
FIG. 8 is a schematic side view showing in further detail the primary components of a preferred embodiment of the centrifugal fraction collection system shown in FIG. 2.
Figure 9A:
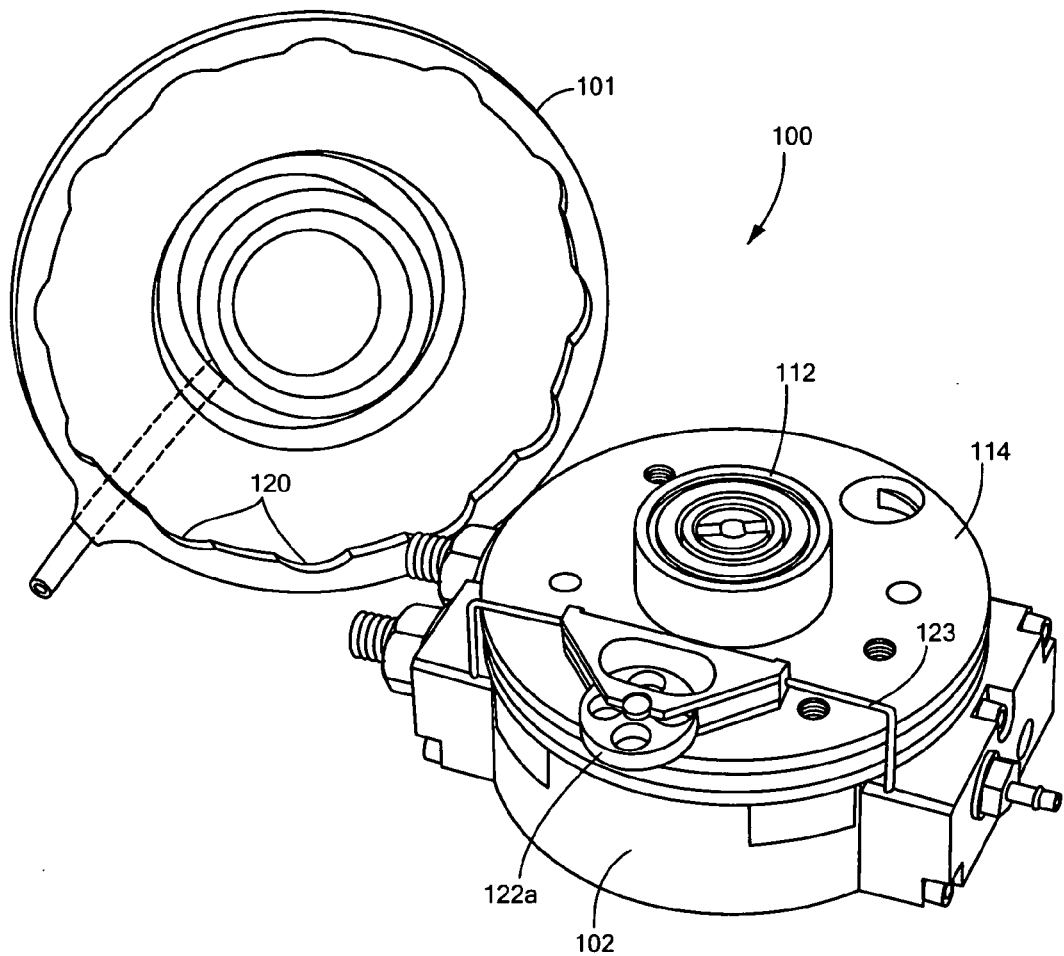
FIGS. 9A, 9B, 9C, and 9D are three-dimensional views showing in further detail exemplary embodiments of the primary components of the distributor subsystem shown in FIGS. 7A, 7B, and 8.

FIG. 9A, where like parts have been given like numbers, shows in further detail the primary components of one exemplary embodiment of distributor subsystem 100 with actuator 102, rotating plate 114, and Sprag clutch 112. In this example, actuator 102 is pneumatically activated by a high pressure pneumatic pulse provided via port 108, FIG. 8, and plenum supply 109 delivered to actuator 102 by passages 106 and 107. Rotating pawl 122*a*, FIG. 9A, is flexibly attached to actuator 102 by flexible wire 123. Distributor cover 101 preferably includes a plurality of detent recesses 120 that receive rotating pawl 122*a* to lock distributor cover 101 of distributor subsystem 100 in place.

Figure 9B:
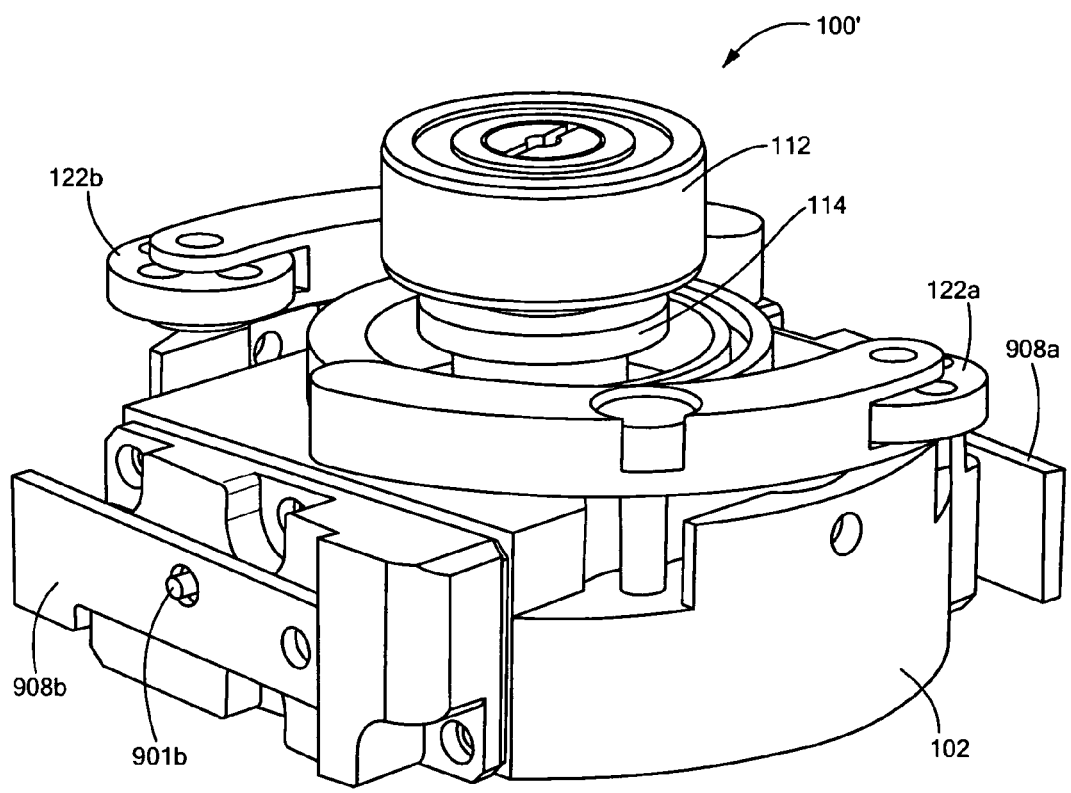

FIG. 9B, where like parts have been given like numbers, shows another embodiment of distributor subsystem 100' which preferably includes actuator 102, rotating plate 114, and Sprag clutch 112. In this example, two rotating pawls 122*a*, 122*b*, are fitted to the top of actuator 102. This provides a more reliable locking to distributor cover 101, FIG. 9C, when distributor 100', FIG. 9B, is rotated to the next collection container. In this example, the two rotating pawls 122*a*, 122*b* engage two of the recesses 120, FIG. 9C, instead of only one, as shown in FIG. 9A with single pawl roller mechanism 122*a*.

Figure 9C:
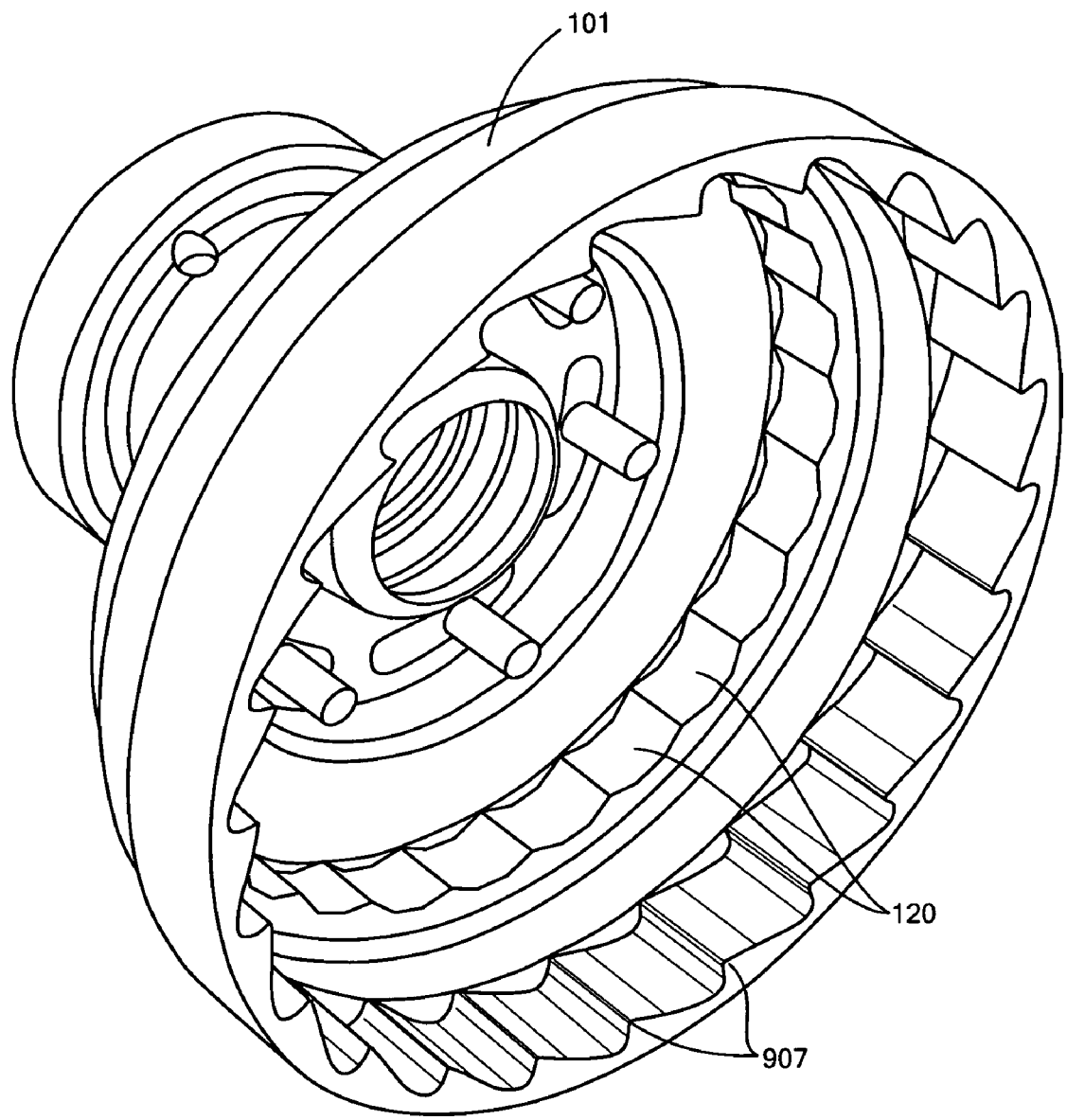
Figure 9D:
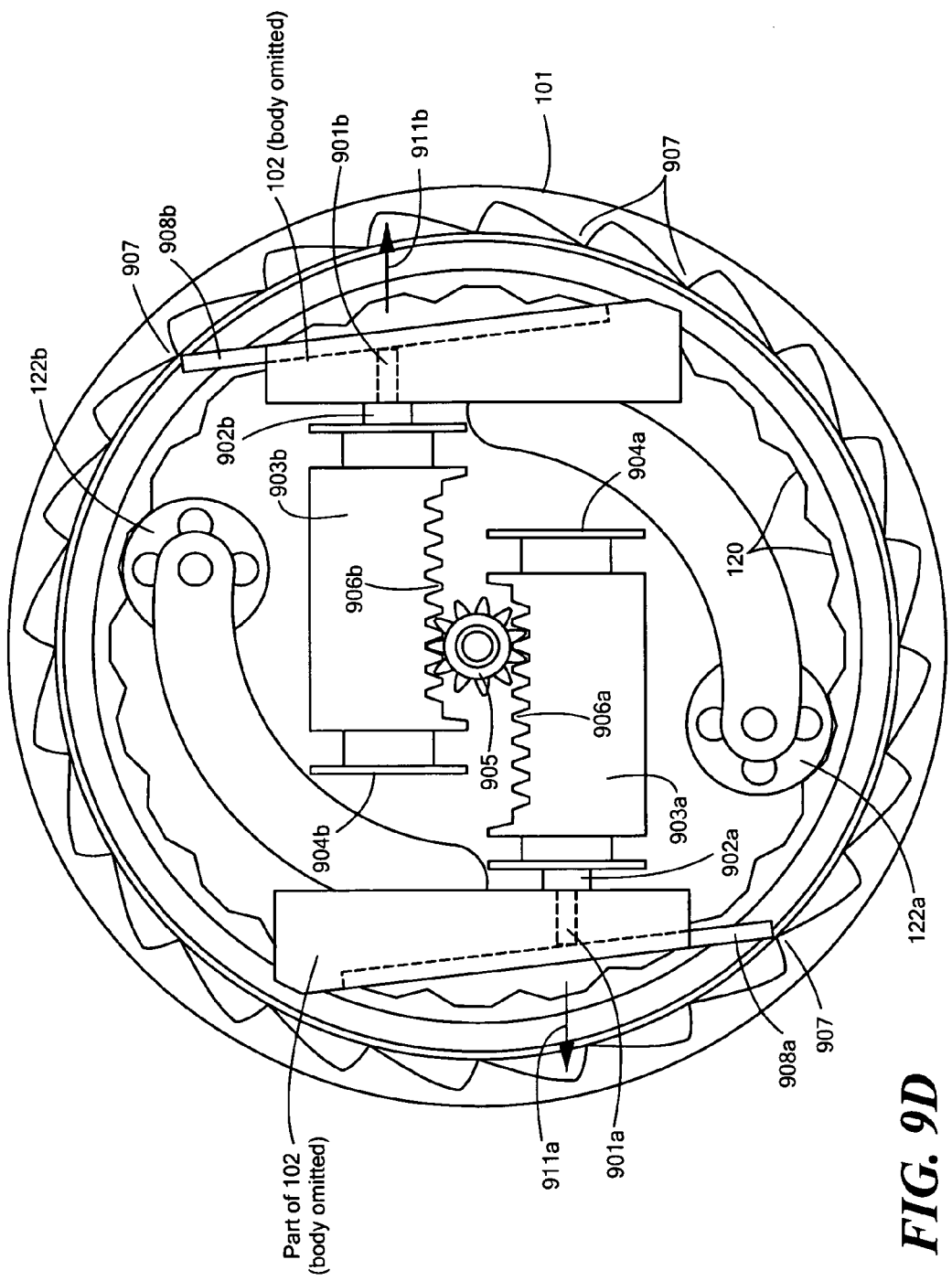

FIG. 9D, where like parts have been given like numbers, shows the primary components of one design of actuator 102, FIG. 9B. In this example, actuator 102 includes dowel pins 901*a* and 901*b* (shown in phantom) fitted to the ends of piston spring guides 902*a* and 902*b* located within rotary actuator pistons 903*a* and 903*b*. When pneumatic pressure is applied to rotary actuator 102 to cause distributor subsystem 100 to index (discussed below), piston ends 904*a* and 904*b* are forced to drive center pinion gear 905 with integral rack gears 906*a* and 906*b*. As actuator pistons 903*a* and 903*b* are driven to their limit of travel, dowel pins 901*a* and 901*b* extend from the rotary actuator 102 to make interference contact with stopping lever 908*a* and 908*b* which makes interference contact with distributor cover 101 and stopping teeth 907, as shown by arrows 911*a* and 911*b*, coincident with flexible eluant tube 158, FIG. 8, reaching the intended collection container 146. In this way, distributor cover of distributor subsystem 100 and 100' 101, FIGS. 7A, 7B, and 8, are brought to an abrupt halt at the correct next collection container 146 despite the angular momentum which has accumulated within distributor subsystem 100 during indexing, which may exceed the capability of the rotating pawl(s) 122*a*, 122*b*, FIG. 9B to overcome. This prevents the flexible eluant tube 158, FIGS. 7A, 7B, and 8, from overshooting the intended next collection container 146. When the pneumatic pressure is removed, the rotary actuator pistons 903*a* and 903*b*, FIG. 9D, are pushed back to their original starting position by springs (not shown) installed over the spring guides 902*a* and 902*b*, inside the pistons 903*a* and 903*b*. During this time Sprag clutch 112, FIG. 9B, allows the pinion gear 905, FIG. 9D, to rotate freely without affecting the position of the distributor cover 101. The rotating pawl(s) 122*a*, 122*b*, FIGS. 9B, and 9D, assure that the distributor cover 101, FIGS. 7A, 7B, and 8, remain pointed at the intended collection container 146 during this rotary actuator resetting process by engaging detent recesses 120.

Although, as discussed above, distributor subsystem 100 is advanced to a next predetermined sample collection container using actuator 102 which is powered pneumatically, this is not a necessary limitation of this invention as any type of actuator known to those skilled in the art may be used, as actuator 102 may be electrically or mechanically powered and controlled by electrical signals, wireless signals, or optical signals, or electromagnetic signals.

In operation, distributor subsystem 100, FIGS. 7A, 7B, and 8, with guide 156 and flexible eluant tube 158 is aligned with a first sample collection container, e.g., sample collection container 144*a* at location 1, FIG. 7A. Rotating carrier 144 is then rotated at sufficient speed to induce the centrifugal force required to separate and retain any of the non-volatile sample components in the eluant sprayed into sample collection container 144*a*. Once the desired amount of the non-volatile components in the eluant has been collected in sample collection container 144*a*, and while rotating carrier 144 is still rotating, distributor subsystem 100 advances guide 156 with flexible eluant tube 158 therein to a next predetermined sample collection container, e.g., sample collection container 144*b* at location 2. Distributor subsystem 100 is advanced by applying the pneumatic pressure pulse by port 108, FIG. 8 which is delivered to actuator 102 by passages 106 and 107. The pneumatic pressure pulse causes actuator 102 to advance distributor subsystem 100 and distributor cover 101, FIGS. 7A, 7B, and 8, guide 156 and flexible eluant tube 158 to the next desired sample collection container, e.g., container 146*b*, FIG. 7A. Once in place at the next desired location, rotating pawl 122*a*, FIG. 9A, or rotary pawls 122*a* and 122*b*, FIG. 9B, engages one of recesses 120 in distributor subsystem 100 to hold distributor subsystem 100 in place at the next location, e.g. location 146*b*, FIG. 7A. Interfering pins 901*a* and 901*b* and stopping levers 908*a* and 908*b*, as discussed above with reference to FIG. 9D, may also be used to stop distributor cover 101 using stopping teeth 907. Recesses 120, FIGS. 9A and 9C, are designed to ensure flexible eluant tube 158 in guide 156 on distributor cover 101 directs the eluant therein proximate the center of the desired sample collection container, e.g., container 146*b*, FIG. 7A. As the pressure in passages 106 and 107, FIG. 8, subsides, rotating plate 114 on actuator 102 begins to return to its original position. In one design, springs (not shown) inside actuator 102 are used to return rotating plate 114 to its original position. At this point, Sprag clutch 112 disengages and slips to allow distributor cover 101, guide 156, and flexible eluant tube 158 to remain at their at its new location, e.g., at sample collection container 144b, FIG. 7A. The process is repeated for the remaining sample collection containers in the rotating carrier, e.g., sample collection containers 146c-146l.

In a preferred design, the next predetermined sample collection container which receives the eluant is located approximately opposite the sample collection container that is currently receiving the flow of eluant, e.g., about 150° when rotating carrier 144 holds 12 collection containers. If rotating carrier 144 holds a different number of collection containers, e.g. 24, then the 150° angle will become 165°, as known by those skilled in the art. This is done to maintain centrifugal balance of the eluant in the plurality of sample collection containers in rotating carrier 144.

For the example shown in FIG. 7A, sample collection container 146b is located about 150° from sample collection container 146a. Distributor subsystem 100 advances distributor cover 101, guide 156, and flexible eluant tube 158 to each of sample collection containers 144a-144l in a predetermined pattern and in a repeatable fashion so that there are no repeats and no omitted sample collection containers in 11 activation events. Only a certain number of sample collection containers are mathematically compatible with such a predetermined pattern, e.g., 12, 24, or 36 sample collection containers, as discussed above. Table 1 below shows one example of the sequence of sample collection containers accessed if rotating carrier 144 holds twelve equally spaced sample collection containers, e.g., sample collection containers 146a-146l and distributor subsystem 100 advances 150° for each fraction:

TABLE 1

Pattern of fraction collection in rotating carrier 144 with 12 collection containers 146a-146l.

| Fraction Sequence | Container Degrees Total | Container Degrees From Start | Container Location From Start |
|---|---|---|---|
| 1 | 0 | 0 | 1 |
| 2 | 150 | 150 | 6 |
| 3 | 300 | 300 | 11 |
| 4 | 450 | 90 | 4 |
| 5 | 600 | 240 | 9 |
| 6 | 750 | 30 | 2 |
| 7 | 900 | 180 | 7 |
| 8 | 1050 | 330 | 12 |
| 9 | 1200 | 120 | 5 |
| 10 | 1350 | 270 | 10 |
| 11 | 1500 | 60 | 3 |
| 12 | 1650 | 210 | 8 |
| 13 | 1800 | 0 | 1 |

In one design, centrifugal fraction collection system 140, FIGS. 2-9D, preferably includes collection container identification subsystem 250, FIG. 8, determining which of the sample collection containers, e.g., sample collection containers 146a-146l, FIG. 7A, is receiving the eluant from flexible eluant tube 158 while rotating carrier 144 is rotating at about 1,500 r.p.m. Collection container identification subsystem, 250, FIG. 8, includes rotating carrier sensor 252, e.g., a Hall effect sensor, disposed in housing 142 that detects target 254, e.g., a permanent magnet. Target 254 may be placed on rotating carrier 144 proximate of the first sample collection containers to receive the eluant, sample collection container 146a, FIG. 7A, at location 1. Thus, for each rotation of rotating carrier 144, sensor 252 will detect target 254 and the location of sample collection container 146a at location 1. Collection container identification system 250 also includes distributor cover sensor 256 and cable 257, e.g., Hall effect sensor, that detects target 258, e.g., a permanent magnet. Target 258 is disposed on distributor cover 101 at a predetermined location relative to detent recesses 120 such that proximity signals from targets 254, 258 never coincide. Therefore, for each rotation of rotating carrier 144, distributor sensor 256 detects target 258 on distributor cover 101. A calculation is performed to determine by what percentage the time from the rotating carrier target 254 to the distributor cover target 258 is relative to the total revolution time as determined by the time between two consecutive proximity signals from the rotating carrier target 254.

Figure 10A:
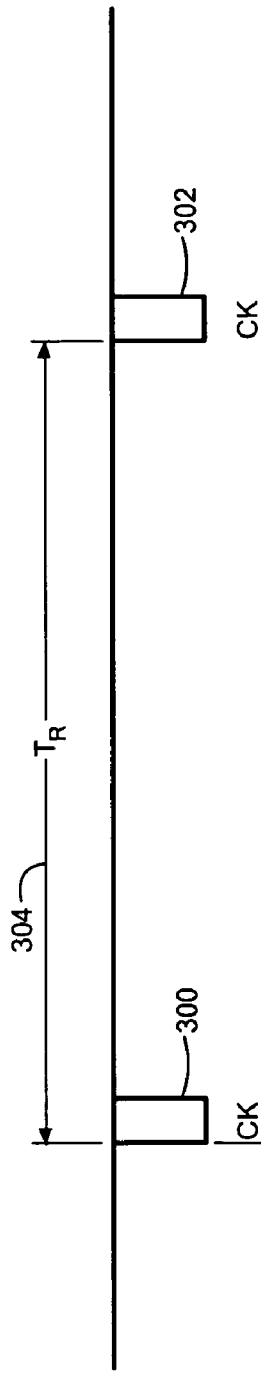
FIGS. 10A and 10B are timing diagrams showing the carrier pulses generated by the detector subsystem shown in FIG. 8 used to determine to which sample collection container the guide and the flexible eluant tube are located.

For example, rotating carrier sensor 252 detects target 254 and generates carrier target proximity pulse 300, FIG. 10A when the target on the rotating carrier 144 passes the sensor 252 initially and carrier target proximity pulse 302 the second time the target 254 passes the sensor 252. The period, $T_R$, between pulses 300 and 302 is indicated at 304. Therefore, the time rotating carrier 144, FIG. 8, takes to make one revolution is known, e.g., $T_R$=40 msec when the carrier is turning at 1,500 r.p.m. Simultaneously with the above determination of the period of the rotating carrier, the elapsed time between the initial proximity signal caused by target 254, discussed above, and the occurrence of the proximity signal from the distributor cover target 258 is recorded.

Figure 10B:
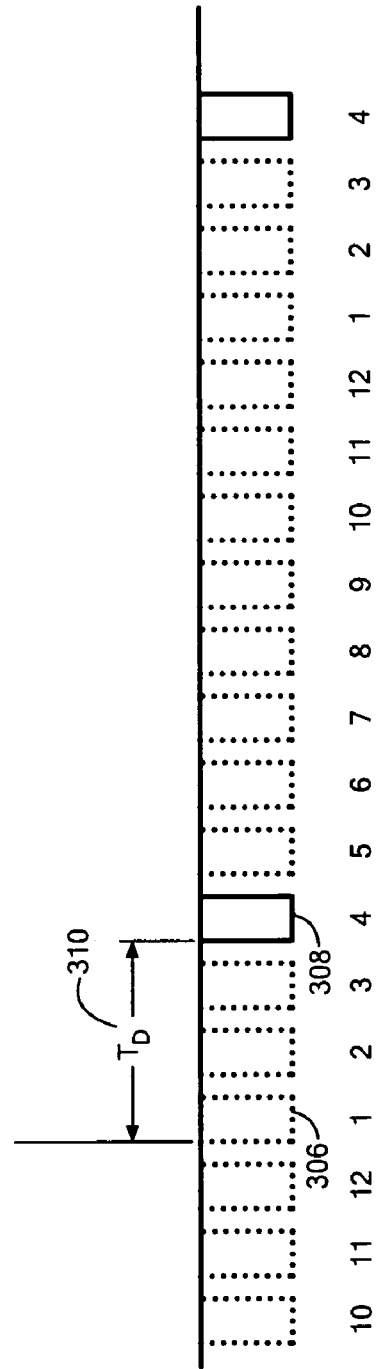

To determine the position of the sample collection container at which distributor cover 101 with flexible eluant tube 158 is currently located, collection container identification subsystem 250 determines the time difference between the detection of target 254 by rotating carrier sensor 252, e.g., pulse 300, FIG. 10A, and the detection of target 258, FIG. 8, by distributor sensor 256, e.g., pulse 308, FIG. 10B. For example, when distributor cover 101, guide 156, and flexible eluant tube 158, FIG. 7A, are at positioned at any sample collection containers 144a-144l, distributor sensor 258, FIG. 8, will generate a particular pulse 308, FIG. 10B. The time, or period, between carrier pulse 300, FIG. 10A, and distributor pulse 308, is measured, e.g., 14.8 msec, as shown by $T_D$ 310.

TABLE 2

Sensor quotient to container sequence look-up

| Detent Location | Sensor Quotient | Fraction Container |
|---|---|---|
| 1 | 0.04 | 1 |
| 2 | 0.12 | 6 |
| 3 | 0.21 | 11 |
| 4 | 0.29 | 4 |
| 5 | 0.37 | 9 |
| 6 | 0.46 | 2 |
| 7 | 0.54 | 7 |
| 8 | 0.62 | 12 |
| 9 | 0.71 | 5 |
| 10 | 0.79 | 10 |
| 11 | 0.87 | 3 |
| 12 | 0.96 | 8 |

The sensor quotient is obtained by dividing the distributor cover 101 target time by the period of rotational carrier 144 to obtain a fractional sensor quotient. The magnitude of this sensor quotient is proportional to the position of the guide 156 on the rotational carrier 144. Now that collection container identification subsystem 250 has determined the quotient associated with the position of distributor cover 101, guide 156 and flexible eluant tube 158, a translation of the sensor quotient to the collection sequence is determined using the "Sensor Quotient" and "Fraction Container" columns of Table 1 above. The data of this table are specific to the number of containers in a rotating carrier and the relative position of the two proximity targets. For a given set of parameters, this table is programmed into an internal controller of fraction collector system 140' (discussed below) for use in displaying the current collection container and to detect a failure of the distributor subsystem 100 to access the collection containers in the intended sequence.

The sequence number of the collection container needs to be determined in this manner so that the value can be reported to the instrument operator and software system (discussed below). Because the actual collection event can not be visually observed it is important to the validity of the collection process that confirmation of the intended sequence be made.

In this example, the period between carrier pulse 300 and distributor pulse 308, $T_D$, is equal to 14.8 msec. $T_D$ is divided by $T_R$ (40 msec) which yields a quotient of 0.37. As shown in Table 2 above, the fourth container position produces a quotient value equal to 0.37. Therefore, this position is associated with sample container 9 in the collection sequence.

As discussed above with reference to FIG. 2 and FIGS. 3A-3B, end 162 of flexible eluant tube 158 preferably extends into sample collection container 146 to increase the yield of the fractionated sample in sample collection container 146. In order to accommodate this feature, distributor subsystem 100 FIG. 8, includes retraction device 200. Retraction device 200 retracts end 162 of flexible eluant tube 158 from the sample collection container 146 currently receiving the flow of eluant, e.g., sample collection container 146a, FIG. 7, before distributor subsystem 100 advances to a next predetermined sample collection container, e.g., sample collection container 146b at location 2. After distributor subsystem 100 has advanced to the next predetermined sample collection container, retraction device 200, FIG. 8 extends end 162 of flexible eluant tube 158 into the next predetermined sample collection container.

Figure 11:
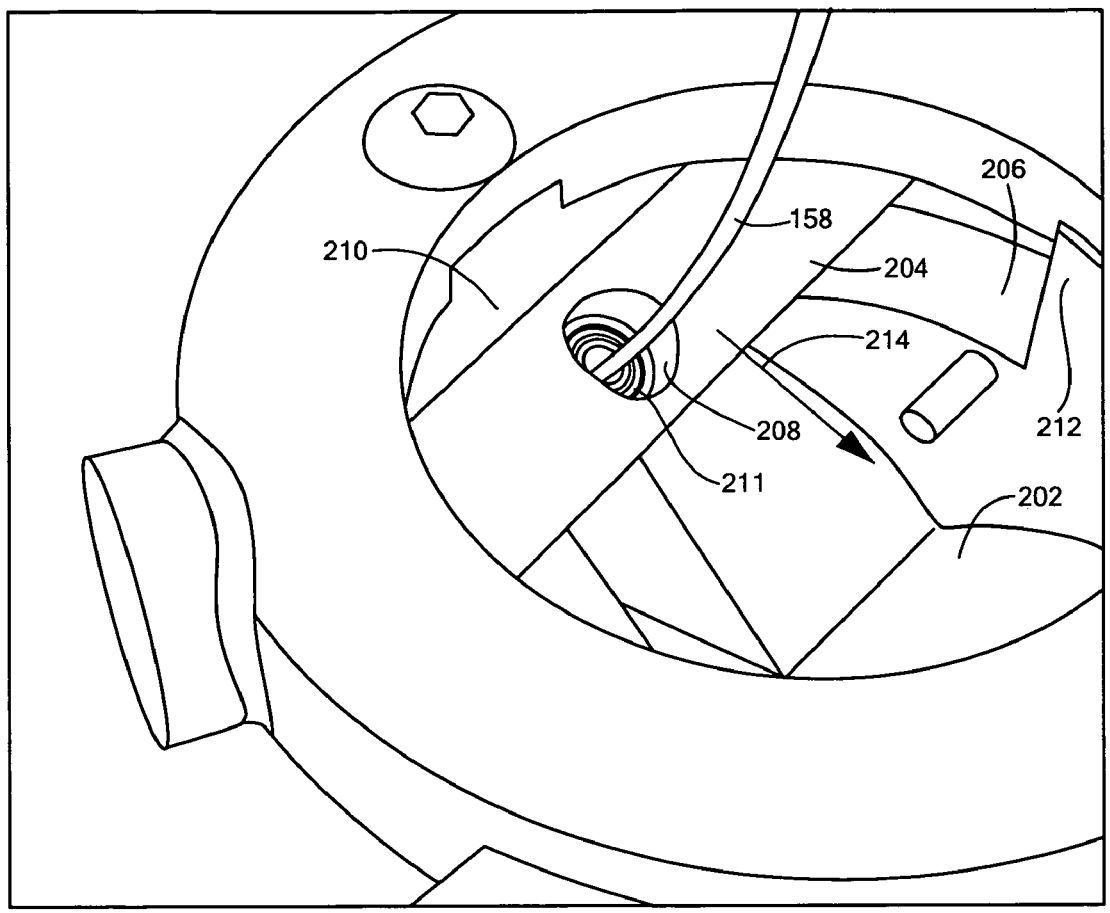
FIG. 11 is a three-dimensional side view showing in further detail one embodiment of the retraction system shown in FIG. 8.

In one design, retraction device 200 includes V-shaped piston-actuator 202 and roller 204 disposed in slot 206 in distributor cover 101. Roller 204, shown in greater detail in FIG. 11, where like parts have been given like numbers, includes orifice 208 which can be fitted with a bearing 211 to prevent wear on the outer diameter of flexible eluant tube 158. Flexible eluant tube 158 is disposed through orifice 208. A pneumatic pressure pulse provided by port 108, FIG. 8 and delivered by passages 106 and 107 to piston-actuator 202 drives piston-actuator 202 in an upward direction to the location shown at 203. The V-shape of piston-actuator 202 causes dowel pin roller 204 in slot 206 to transversely move from its location against wall 210 of slot 206 to wall 212, as shown by arrow 214, FIG. 11. This causes end 162, FIG. 8, of flexible eluant tube 158 to be retracted from sample collection container 146, FIG. 7A. Then, distributor subsystem 100 advances guide 156 and flexible eluant tube 158 to the next predetermined sample collection container. Once in place at the next desired sample collection container, distributor subsystem 100 and distributor cover 101 is locked in position, as discussed above with reference to FIGS. 8 and 9A-9D. At this time, the pressure reduces in passages 106 and 107, FIG. 8, and piston-actuator 202 lowers to its original position. Roller 204 is therefore allowed to return to its original position against wall 210 of slot 206. Centrifugal force $F_c$ 150 on the roller and the tendency of eluant tube 158 to straighten provide the force to return the roller to its original position. Elimination of the bend in eluant tube 158 allows end 162 of flexible eluant tube 158 to extend into the next desired sample collection container, e.g., sample collection container 146b, FIG. 7A.

In another design, a piston (not shown) could also be located within spindle 151, FIG. 8, to reduce the complexity of the pneumatic passages and to reduce the consumption upon the pressurized supply of pneumatic power. An appropriately sized dowel pin positioned between the top of a piston located in spindle 151 and the bottom of the V-shaped piston-actuator 202 would translate vertical piston motion to vertical V-shaped actuator motion.

Although as shown in FIG. 8, retraction device 200 utilizes a pneumatic pulse to activate piston 202, this is not a necessary limitation of this invention, as piston 202 may be driven-electronically or mechanically and be controlled by electronic signals, wireless signals, optical signals, or by electromagnetic signals, as know by those skilled in the art.

Figure 12:
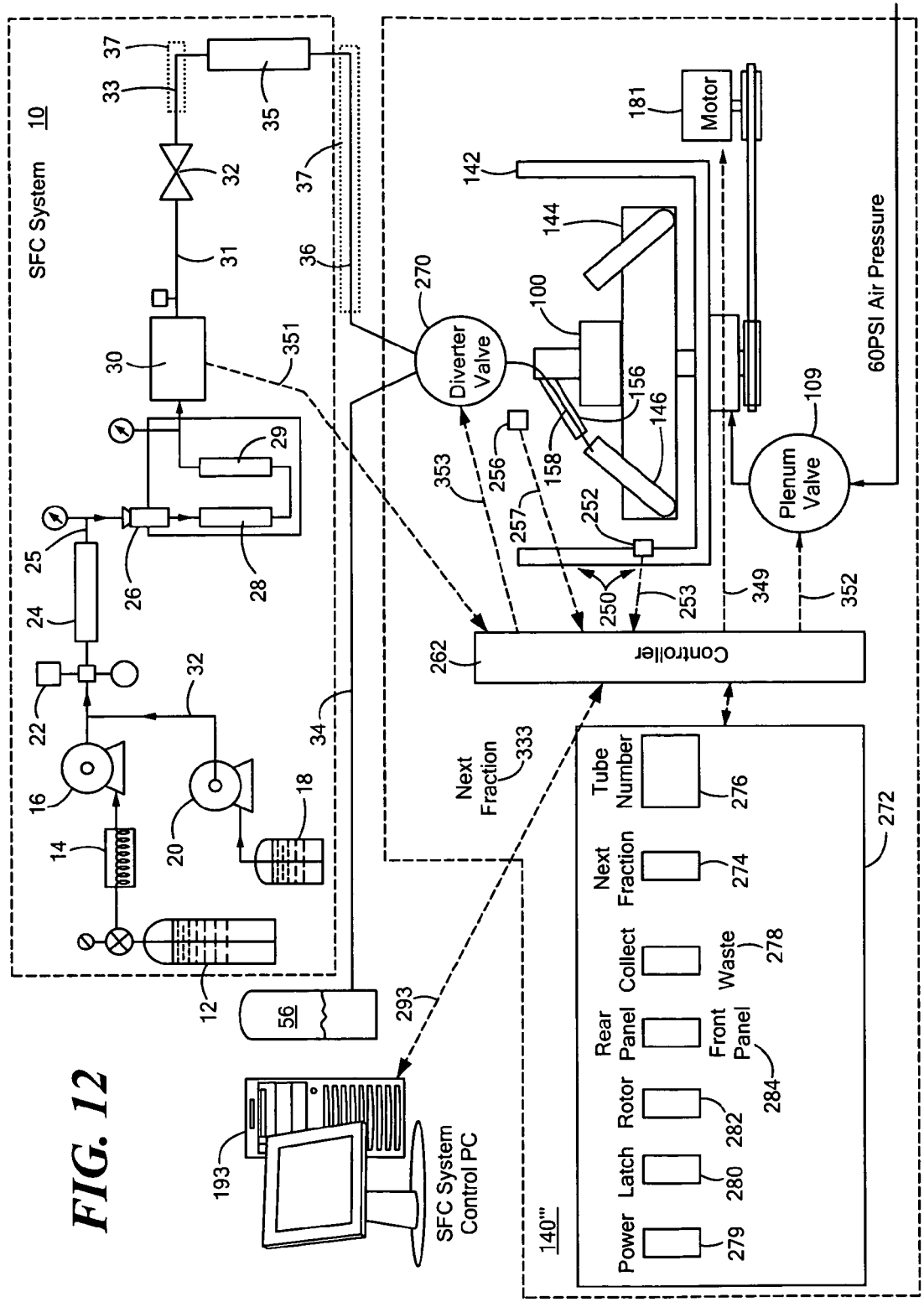
FIG. 12 is a schematic view showing an exemplary computer subsystem and controller of this invention used to control the centrifugal collection system shown in FIGS. 2-11 and an SFC system.

In one embodiment, centrifugal fraction collection system 140''', FIG. 12 of this invention, includes diverter valve 270 which directs the flow of eluant in tube 36 from SFC system 10 to collection system 140''' or to waste collection container 56 via tube 34. Diverter valve 270 operates in combination with distributor subsystem 100 to deliver the flow of eluant to either waste collection container 56 or to flexible eluant tube 158 which directs the flow of eluant to collection container 146, e.g., a desired one of a plurality of collection containers shown in FIGS. 7A and 7B. Diverter valve 270, FIG. 12, is driven by controller 262 by line 353 which responds to signals from a computer subsystem, e.g., computer subsystem 193, similar as discussed above with reference to FIG. 6, connected to controller 262, FIG. 12, to direct the eluant to flow to waste collection container 56, or flexible eluant tube 158. In addition, when the computer subsystem 193, sends a NEXT FRACTION command 333 by connection 293 to the controller 262, plenum supply 109 (also shown in FIG. 8) is energized via connection 352 to cause the distributor subsystem 100 to index the eluant tube 158 to the next predetermined collection container 146, e.g., 150° in rotating carrier 144, FIG. 7A, having 12 collection containers. During the time of indexing flexible eluant tube 158, controller 262 also directs the diverter valve 270 via connection 353 to momentarily, e.g., about 0.5 seconds, block the flow of eluant from SFC system 10 to prevent contamination of the collection containers not intended for collection of the current fraction. The flow of eluant is momentarily stopped before retraction device 200, FIG. 8, retracts flexible eluant tube 158 from sample collection container 146 that has been receiving the eluant and before distributor subsystem 100 advances guide 156 and flexible eluant tube 158 to the next predetermined sample collection container. This prevents contamination of sample collection containers, e.g., sample collection containers 144a-144l, FIG. 7A during advancement of distributor subsystem 100.

When diverter valve 270 is not in the collect or stop flow position, tube 34 dispenses the eluant to a waste container 56. The flow of eluant is diverted to waste collection container 56 or to the next collection container when a predetermined amount of sample has been collected (fractionated) in a predetermined sample collection container receiving the flow of eluant. Preferably, diverter valve 270 is controlled by controller 262, e.g., an internal PCB, coupled to a computer subsystem 193 which may also control SFC system 10. These command signals are sent to controller 262 inside fraction collector 140''' via connection 293.

Controller 262 also controls rotating carrier 144 by line 349 connected to motor 181, the advancement of distributor subsystem 100 and operation of retraction device 200, FIG. 8, by connection 352, FIG. 12, powering plenum supply valve 109. In other designs, controller 262 may control advancement of distributor subsystem 100 and operation of retraction device 200 with electrical signals, wireless signals, optical signals, or electromagnetic signals, as known by those skilled in the art. Controller 262 receives signal from collection container identification subsystem 250 by lines 253 and 257. Controller 262 coupled to computer subsystem 193 also processes signals from detector 30 of SFC system 10 by line 351, as discussed above with reference to FIG. 8, for recognizing when separated compound aliquots transition in the flow path so that changes in collection container might be automatically triggered by controller 262, FIG. 12. In this way, each pure compound from the SFC separation process is trapped in different collection containers.

Collection system 140''' preferably includes control panel 272. Control panel 272 typically includes switch 274 for activating the next fraction to one of the plurality of sample collection containers, e.g. sample collection containers 144a-144l, FIG. 7A. Display 276, FIG. 12, shows the current sample collection container receiving the eluant as determined by the collection container identification subsystem 250, FIGS. 8 and 12. Switch 278, FIG. 12, controls diverter valve 270, FIGS. 8 and 12, to receive the flow of eluant into collection container 146 or dispose of the flow of eluant into waste collection container 56. Switch 279 activates power and switch 282 activates rotating carrier 144. Latch button 280 activates a locking mechanism (not shown) to ensure cover 171, FIGS. 2, 5, and 8, cannot be opened during operation. Switch 284 switches between automatic control of internal controller 262, by computer subsystem 193 and manual mode, which activates switches 274 and 278 for manual operation of diverter valve 270, and distributor subsystem 100.

Although, as discussed above with reference to FIGS. 2-12, centrifugal collection system 140 preferably operates at atmospheric pressure, e.g., about 14.7 p.s.i., this is not a necessary limitation of this invention, as system 140 may also operate in vacuum conditions to promote rapid drying of fractions, as known by those skilled in the art.

Figure 13:
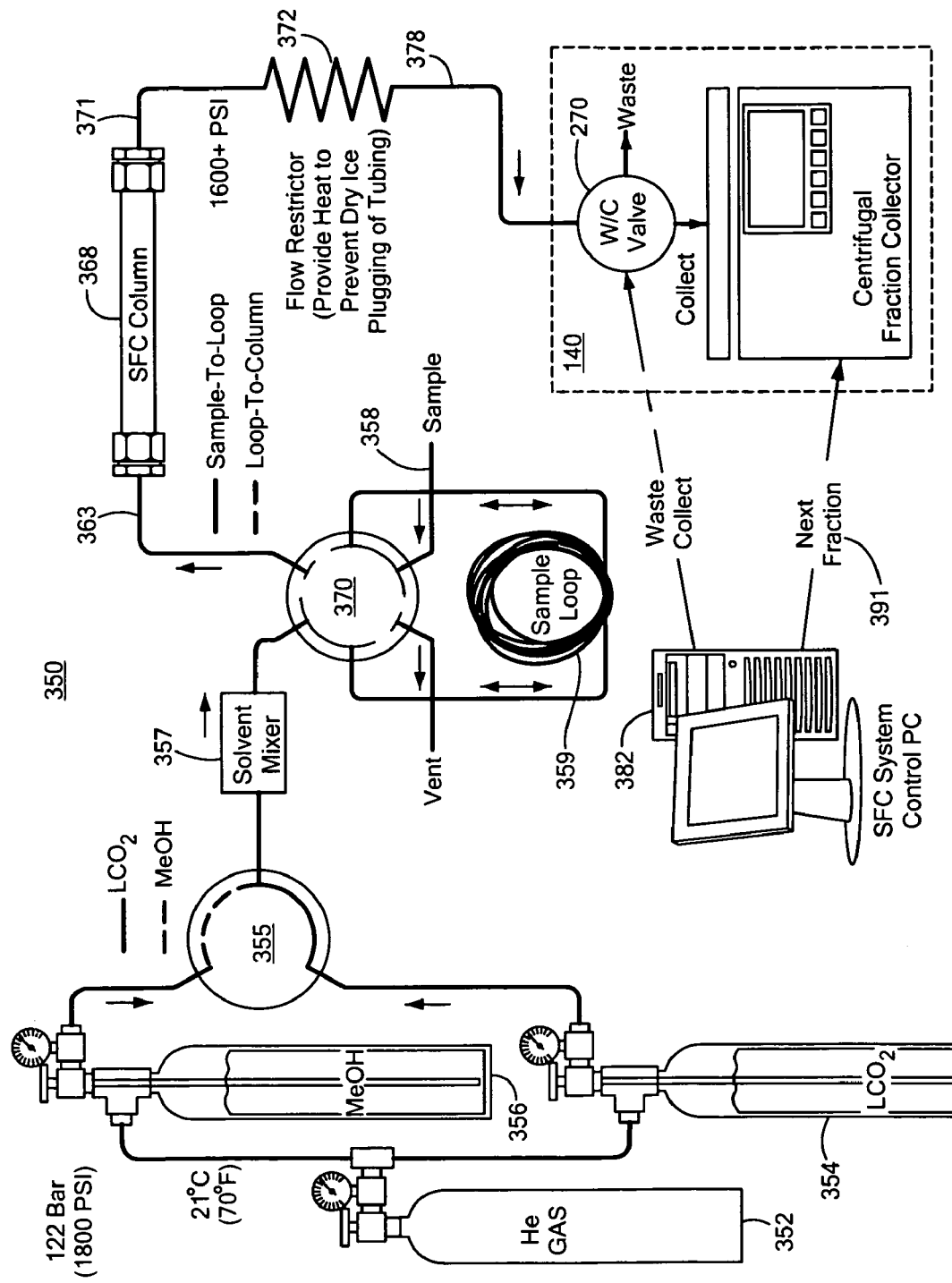
FIG. 13 is a schematic diagram showing the primary components of one embodiment of a flash supercritical fluid chromatography system of this invention.

Flash super critical fluid chromatography centrifugal fraction collection system 350, FIG. 13 of this invention, where like parts have been given like numbers, includes tank 352 of pressurized gas, e.g., helium, tank 354 of pressurized volatile components, e.g., carbon dioxide, and tank 356 of an organic modifier, e.g., methanol. Selector valve or proportioning valve 355 couples flow from tanks 354 and 356. Mixer 357 mixes the proportional aliquots of volatile component (carbon dioxide) and the organic modifier (methanol) delivered from proportioning valve 355. Injector subsystem 370 includes sample port 350 which 358 introduces liquid sample components into the high pressure flow stream in tube 363 via sample loop 359 of injector subsystem 370. Chromatography column 368 is connected to six-port injection valve 370 and receives the flow of mixed supercritical $CO_2$ and organic modifier into which an aliquot of sample has been inserted with injection valve 370 by line 363. Phase transition tube 372, e.g., a restriction capillary, receives the separated sample traveling in the eluant stream from chromatography column 368 and reduces the pressure in tube 371 from about 1,600 p.s.i. to atmospheric pressure (e.g., about 14.7 p.s.i.) in tube 378. Diverter valve 270, similar as discussed above with reference to FIGS. 8 and 12, is coupled to tube 378. Centrifugal fraction collection system 140, FIG. 13 fractionates the sample in the flow of eluant in line 378, similarly as discussed above with reference to FIGS. 2-12. Flash computer system 382, FIG. 13, controls in addition to those functions discussed above with reference to computer subsystem 193, FIG. 12, 3-way proportioning valve 355. Flash SFC system 350 provides high fraction count capability, e.g., more than the 4 to 8 fractions typically provided on SFC systems. Flash SFC system 350 is a low cost, highly productive personal separation system for low resolution clean-up separations on crude reaction products and complex mixtures. A key benefit of system 350 is inherent dryness of the resultant fraction containers because the fractions are processed with supercritical carbon dioxide which is vented as a part of the centrifugal fractionation process. SFC fractions generally require little drying time before being ready for the next processing step.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A centrifugal fraction collection system comprising:
    a rotating carrier for holding at least one sample collection container and inducing a centrifugal force;
    a guide disposed on the rotating carrier; and
    a flexible eluant tube disposed over the rotating carrier and through the guide for receiving a flow of eluant having volatile and non-volatile components and directing the flow of eluant into at least one sample collection container wherein the centrifugal force separates the non-volatile and volatile components based on their respective densities and collects the non-volatile components in at least one sample collection container.

2. The system of claim 1 in which one end of the flexible eluant tube is configured to receive the flow of eluant from a supercritical fluid chromatography system.

3. The system of claim 1 in which the one end of the flexible eluant tube is maintained in a fixed position above the rotating carrier and the other end of the flexible eluant tube axially rotates in the guide.

4. The system of claim 1 further including a plurality of sample collection containers disposed in the rotating carrier.

5. The system of claim 4 in further including a distributor subsystem coupled to and synchronized with the rotating carrier for locating, aligning, and locking the flexible eluant tube to a predetermined one of the plurality of sample collection containers and for distributing fractions of the eluant to a predetermined number of the plurality of sample collection containers.

6. The system of claim 5 in which the next predetermined sample collection container in the collection sequence is located approximately opposite a sample collection container receiving a flow of eluant and for maintaining asymmetrical distribution of weight of collected eluant among the plurality of sample collection containers.

7. The system of claim 6 in which the distributor subsystem advances the guide and flexible eluant tube to each of the plurality of sample collection containers in a predetermined pattern for maintaining a symmetrical distribution of weight of the fractionated eluant in the plurality of sample collection containers.

8. The system of claim 7 further including a collection container identification subsystem for determining the location of one of the plurality of sample collection containers receiving the flow of eluant.

9. The system of claim 5 in which distributor subsystem includes a distributor cover having one or more detent recesses, an actuator, one or more rotating pawls, and a clutch mechanism.

10. The system of claim 9 in which the actuator is coupled to the rotating carrier and the one or more rotating pawls engage the one or more detent recesses in the distributor cover to lock the distributor cover at a desired location.

11. The system of claim 10 in which a profile of the one or more detent recesses in the distributor cover aligns the distributor cover, the guide, and the flexible eluant tube proximate a predetermined one of the plurality of sample collection containers.

12. The system of claim 9 in which the distributor subsystem includes a distributor cover having a plurality of locking teeth and one or more locking pins or levers which engage one or more of the plurality of locking teeth to halt the distributor cover at a desired location and counteract accumulated angular momentum generated by rotating the distributor cover.

13. The system of claim 5 in which the distributor subsystem is advanced to the next predetermined sample collection container mechanically and/or electrically by applying pneumatic pressure pulses and/or by applying mechanical forces and/or by applying electrical signals and/or by applying optical signals and/or by applying wireless signals and/or by applying electromagnetic signals.

14. The system of claim 5 further including a retraction device for retracting the flexible eluant tube from one of the plurality of collection containers while the distributor subsystem advances to the next predetermined one of the plurality of sample collection containers.

15. The system of claim 14 in which the retraction device is controlled mechanically and/or electrically by applying pneumatic pressure pulses and/or by applying mechanical forces and/or by applying electrical signals and/or by applying wireless signals and/or by applying optical signals and/or by applying electromagnetic signals.

16. The system of claim 14 further including a diverter valve coupled between a source of the flow of eluant and the flexible eluant tube configured to temporarily stop the flow of eluant while the retraction device retracts the flexible eluant tube and the distributor subsystem advances the flexible eluant tube to the next predetermined sample collection container and extends the flexible eluant tube into a next predetermined sample collection container and thereafter allowing the flow of eluant to be dispensed in the next predetermined sample collection container.

17. The system of claim 16 further including an embedded controller for controlling the distributor subsystem, the retraction device, the collection container identification subsystem, the diverter valve, and the rotation speed of the rotating carrier by predetermined commands entered into the controller and/or by commands received from an external system control subsystem.

18. The system of claim 17 in which the controller includes a control panel having a display for displaying the sample collection container receiving the eluant and a plurality of switches for controlling operation of the rotating carrier, the distributor subsystem, the diverter valve, and for programming collection of pure compounds from the non-volatile components into one or more of the plurality of collection containers based on a commands entered into the controller and/or signals from a chemical processing system detector and/or from the control computer of a chemical processing system.

19. The system of claim 1 in which the flexible eluant tube extends a predetermined length into a sample collection container for increasing the yield of the non-volatile components.

20. The system of claim 1 in which the volatile components include carbon dioxide and the non-volatile compounds include a component chosen from the group consisting of: molecules, compounds, chiral molecules, enantiomers, drugs, sample precipitates, reactants, reaction products, natural product extracts, and modifier solvents.

21. The system of claim 1 in which the flexible eluant tube is made of a durable material capable of withstanding continuous flexing caused by high speed rotation of the rotating carrier and which is un-reactive with the volatile and non-volatile components.

22. A centrifugal fraction collection system comprising:
a rotating carrier for holding at least one sample collection container and inducing a centrifugal force; and
an eluant tube disposed over the rotating carrier and coupled to the rotating carrier for receiving a flow of eluant having volatile and non-volatile components and directing the flow of eluant into at least one sample collection container wherein the centrifugal force separates the non-volatile and volatile components based on their respective densities and collects the non-volatile components in at least one sample collection container.

23. The system of claim 22 further including a housing, a cover, and a fluidic sealing bearing disposed in the cover, the fluidic sealing bearing including a coupling attached to a rigid eluant tube receiving the flow of eluant and a rotating portion disposed in the coupling fixably attached to a rigid eluant tube which is fixably attached to the rotating carrier.

* * * * *